United States Patent
Jiang et al.

(10) Patent No.: US 11,400,088 B2
(45) Date of Patent: Aug. 2, 2022

(54) USES OF COMPOUND IN PREPARATION OF DRUGS FOR TREATING BRAIN GLIOMA

(71) Applicants: BEIJING PEARL BIOTECHNOLOGY LIMITED LIABILITY COMPANY, Beijing (CN); BEIJING NEUROSURGICAL INSTITUTE, Beijing (CN)

(72) Inventors: Tao Jiang, Beijing (CN); Yanwei Liu, Beijing (CN); Huimin Hu, Beijing (CN); Hepeng Shi, Beijing (CN); Weizhe Xue, Beijing (CN)

(73) Assignees: BEIJING PEARL BIOTECHNOLOGY LIMITED LIABILITY COMPANY, Beijing (CN); BEIJING NEUROSURGICAL INSTITUTE, Beijing (CN)

( * ) Notice: Subject to any disclaimer, the term of this patent is extended or adjusted under 35 U.S.C. 154(b) by 250 days.

(21) Appl. No.: 16/067,549

(22) PCT Filed: Dec. 21, 2016

(86) PCT No.: PCT/CN2016/111227
§ 371 (c)(1),
(2) Date: Jun. 29, 2018

(87) PCT Pub. No.: WO2017/114249
PCT Pub. Date: Jul. 6, 2017

(65) Prior Publication Data
US 2021/0369711 A1    Dec. 2, 2021

(30) Foreign Application Priority Data
Dec. 31, 2015   (CN) .......................... 201511022391.8

(51) Int. Cl.
*A61K 31/5025* (2006.01)
*A61P 35/00* (2006.01)

(52) U.S. Cl.
CPC .......... *A61K 31/5025* (2013.01); *A61P 35/00* (2018.01)

(58) Field of Classification Search
CPC .................................................. A61K 31/5025
See application file for complete search history.

(56) References Cited

U.S. PATENT DOCUMENTS

| | | | |
|---|---|---|---|
| 2006/0009493 A1 | 1/2006 | Koenig et al. | |
| 2011/0294849 A1 | 12/2011 | Lauffer et al. | |

FOREIGN PATENT DOCUMENTS

| | | | |
|---|---|---|---|
| CN | 102448968 | * | 5/2012 |
| CN | 102448968 A | | 5/2012 |
| CN | 103122000 | * | 5/2013 |
| CN | 103122000 A | | 5/2013 |

OTHER PUBLICATIONS

Bao et al Genome Research (2014) No. 11, vol. 24, pp. 1765-1773.*
Bao, Z. S. et al., "RNA-seq of 272 gliomas revealed a novel, recurrent PTPRZ1-MET fusion transcript in secondary glioblastomas," Genome Res., vol. 24, No. 11, Aug. 18, 2014, pp. 1765-1773.
Chen, H. M. et al., "Enhanced expression and phosphorylation of the MET oncoprotein by glioma-specific PTPRZ1-MET fusions", FEBS Letters, vol. 589, No. 13, Apr. 29, 2015, pp. 1437-1443.
International Search Report dated Mar. 7, 2017 for corresponding PCT Application No. PCT/CN2016/111227, with English Translation (6 pages).
Martens, T. et al., "A Novel One-Armed Anti-c-Met Antibody Inhibits Glioblastoma Growth In vivo", Clin Cancer Res, vol. 12, No. 20, Oct. 15, 2006, pp. 6144-6152.
Wen, P.Y. et al., "A phase II study evaluating the efficacy and safety of AMG 102 (rilotumumab) in patients with recurrent glioblastoma", Neuro-Oncology, vol. 13, No. 4, Feb. 4, 2011, pp. 437-446.

* cited by examiner

*Primary Examiner* — Paul V Ward
(74) *Attorney, Agent, or Firm* — Lewis Roca Rothgerber Christie LLP

(57) ABSTRACT

The present invention provides uses of a compound represented by formula A in the preparation of drugs for treating brain glioma and particularly glioblastoma. Particularly provided are uses of the compound represented by formula A in the preparation of drugs for treating expression of specific fusion protein. By means of the technical solution of the present invention, typing of brain glioblastoma can be implemented, a drug administration can be carried out for a specific patient group, and precise treatment can be implemented.

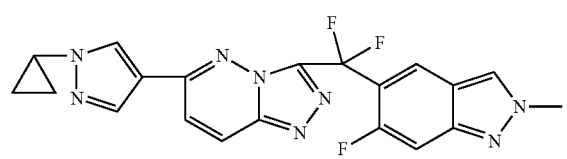

Formula A

22 Claims, 4 Drawing Sheets
Specification includes a Sequence Listing.

SEQUENCE LISTING

```
<160> NUMBER OF SEQ ID NOS: 12

<210> SEQ ID NO 1
<211> LENGTH: 1394
<212> TYPE: PRT
<213> ORGANISM: human
<220> FEATURE:
<223> OTHER INFORMATION: Common c-Met portion of fusion proteins ZM

<400> SEQUENCE: 1
```

Lys Pro Leu Ile Met Lys Ala Pro Ala Val Leu Ala Pro Gly Ile Leu
1               5                   10                  15

Val Leu Leu Phe Thr Leu Val Gln Arg Ser Asn Gly Glu Cys Lys Glu
                20                  25                  30

Ala Leu Ala Lys Ser Glu Met Asn Val Asn Met Lys Tyr Gln Leu Pro
            35                  40                  45

Asn Phe Thr Ala Glu Thr Pro Ile Gln Asn Val Ile Leu His Glu His
        50                  55                  60

His Ile Phe Leu Gly Ala Thr Asn Tyr Ile Tyr Val Leu Asn Glu Glu
65                  70                  75                  80

Asp Leu Gln Lys Val Ala Glu Tyr Lys Thr Gly Pro Val Leu Glu His
                85                  90                  95

Pro Asp Cys Phe Pro Cys Gln Asp Cys Ser Ser Lys Ala Asn Leu Ser
            100                 105                 110

Gly Gly Val Trp Lys Asp Asn Ile Asn Met Ala Leu Val Val Asp Thr
        115                 120                 125

Tyr Tyr Asp Asp Gln Leu Ile Ser Cys Gly Ser Val Asn Arg Gly Thr
    130                 135                 140

Cys Gln Arg His Val Phe Pro His Asn His Thr Ala Asp Ile Gln Ser
145                 150                 155                 160

Glu Val His Cys Ile Phe Ser Pro Gln Ile Glu Glu Pro Ser Gln Cys
                165                 170                 175

Pro Asp Cys Val Val Ser Ala Leu Gly Ala Lys Val Leu Ser Ser Val
            180                 185                 190

Lys Asp Arg Phe Ile Asn Phe Phe Val Gly Asn Thr Ile Asn Ser Ser
        195                 200                 205

Tyr Phe Pro Asp His Pro Leu His Ser Ile Ser Val Arg Arg Leu Lys
    210                 215                 220

Glu Thr Lys Asp Gly Phe Met Phe Leu Thr Asp Gln Ser Tyr Ile Asp
225                 230                 235                 240

Val Leu Pro Glu Phe Arg Asp Ser Tyr Pro Ile Lys Tyr Val His Ala
                245                 250                 255

Phe Glu Ser Asn Asn Phe Ile Tyr Phe Leu Thr Val Gln Arg Glu Thr
            260                 265                 270

Leu Asp Ala Gln Thr Phe His Thr Arg Ile Ile Arg Phe Cys Ser Ile
        275                 280                 285

Asn Ser Gly Leu His Ser Tyr Met Glu Met Pro Leu Glu Cys Ile Leu
    290                 295                 300

Thr Glu Lys Arg Lys Lys Arg Ser Thr Lys Lys Glu Val Phe Asn Ile
305                 310                 315                 320

```
Leu Gln Ala Ala Tyr Val Ser Lys Pro Gly Ala Leu Ala Arg Gln
                325                 330                 335

Ile Gly Ala Ser Leu Asn Asp Asp Ile Leu Phe Gly Val Phe Ala Gln
                340                 345                 350

Ser Lys Pro Asp Ser Ala Glu Pro Met Asp Arg Ser Ala Met Cys Ala
                355                 360                 365

Phe Pro Ile Lys Tyr Val Asn Asp Phe Phe Asn Lys Ile Val Asn Lys
        370                 375                 380

Asn Asn Val Arg Cys Leu Gln His Phe Tyr Gly Pro Asn His Glu His
385                 390                 395                 400

Cys Phe Asn Arg Thr Leu Leu Arg Asn Ser Ser Gly Cys Glu Ala Arg
                405                 410                 415

Arg Asp Glu Tyr Arg Thr Glu Phe Thr Thr Ala Leu Gln Arg Val Asp
                420                 425                 430

Leu Phe Met Gly Gln Phe Ser Glu Val Leu Leu Thr Ser Ile Ser Thr
            435                 440                 445

Phe Ile Lys Gly Asp Leu Thr Ile Ala Asn Leu Gly Thr Ser Glu Gly
        450                 455                 460

Arg Phe Met Gln Val Val Val Ser Arg Ser Gly Pro Ser Thr Pro His
465                 470                 475                 480

Val Asn Phe Leu Leu Asp Ser His Pro Val Ser Pro Glu Val Ile Val
                485                 490                 495

Glu His Thr Leu Asn Gln Asn Gly Tyr Thr Leu Val Ile Thr Gly Lys
                500                 505                 510

Lys Ile Thr Lys Ile Pro Leu Asn Gly Leu Gly Cys Arg His Phe Gln
            515                 520                 525

Ser Cys Ser Gln Cys Leu Ser Ala Pro Pro Phe Val Gln Cys Gly Trp
        530                 535                 540

Cys His Asp Lys Cys Val Arg Ser Glu Glu Cys Leu Ser Gly Thr Trp
545                 550                 555                 560

Thr Gln Gln Ile Cys Leu Pro Ala Ile Tyr Lys Val Phe Pro Asn Ser
                565                 570                 575

Ala Pro Leu Glu Gly Gly Thr Arg Leu Thr Ile Cys Gly Trp Asp Phe
            580                 585                 590

Gly Phe Arg Arg Asn Asn Lys Phe Asp Leu Lys Lys Thr Arg Val Leu
        595                 600                 605

Leu Gly Asn Glu Ser Cys Thr Leu Thr Leu Ser Glu Ser Thr Met Asn
        610                 615                 620

Thr Leu Lys Cys Thr Val Gly Pro Ala Met Asn Lys His Phe Asn Met
625                 630                 635                 640

Ser Ile Ile Ile Ser Asn Gly His Gly Thr Thr Gln Tyr Ser Thr Phe
                645                 650                 655

Ser Tyr Val Asp Pro Val Ile Thr Ser Ile Ser Pro Lys Tyr Gly Pro
            660                 665                 670

Met Ala Gly Gly Thr Leu Leu Thr Leu Thr Gly Asn Tyr Leu Asn Ser
        675                 680                 685

Gly Asn Ser Arg His Ile Ser Ile Gly Gly Lys Thr Cys Thr Leu Lys
        690                 695                 700

Ser Val Ser Asn Ser Ile Leu Glu Cys Tyr Thr Pro Ala Gln Thr Ile
705                 710                 715                 720

Ser Thr Glu Phe Ala Val Lys Leu Lys Ile Asp Leu Ala Asn Arg Glu
                725                 730                 735
```

-continued

```
Thr Ser Ile Phe Ser Tyr Arg Glu Asp Pro Ile Val Tyr Glu Ile His
            740                 745                 750

Pro Thr Lys Ser Phe Ile Ser Gly Gly Ser Thr Ile Thr Gly Val Gly
            755                 760                 765

Lys Asn Leu Asn Ser Val Ser Val Pro Arg Met Val Ile Asn Val His
        770                 775                 780

Glu Ala Gly Arg Asn Phe Thr Val Ala Cys Gln His Arg Ser Asn Ser
785                 790                 795                 800

Glu Ile Ile Cys Cys Thr Thr Pro Ser Leu Gln Gln Leu Asn Leu Gln
                805                 810                 815

Leu Pro Leu Lys Thr Lys Ala Phe Phe Met Leu Asp Gly Ile Leu Ser
            820                 825                 830

Lys Tyr Phe Asp Leu Ile Tyr Val His Asn Pro Val Phe Lys Pro Phe
        835                 840                 845

Glu Lys Pro Val Met Ile Ser Met Gly Asn Glu Asn Val Leu Glu Ile
    850                 855                 860

Lys Gly Asn Asp Ile Asp Pro Glu Ala Val Lys Gly Glu Val Leu Lys
865                 870                 875                 880

Val Gly Asn Lys Ser Cys Glu Asn Ile His Leu His Ser Glu Ala Val
                885                 890                 895

Leu Cys Thr Val Pro Asn Asp Leu Leu Lys Leu Asn Ser Glu Leu Asn
            900                 905                 910

Ile Glu Trp Lys Gln Ala Ile Ser Ser Thr Val Leu Gly Lys Val Ile
        915                 920                 925

Val Gln Pro Asp Gln Asn Phe Thr Gly Leu Ile Ala Gly Val Val Ser
    930                 935                 940

Ile Ser Thr Ala Leu Leu Leu Leu Leu Gly Phe Phe Leu Trp Leu Lys
945                 950                 955                 960

Lys Arg Lys Gln Ile Lys Asp Leu Gly Ser Glu Leu Val Arg Tyr Asp
                965                 970                 975

Ala Arg Val His Thr Pro His Leu Asp Arg Leu Val Ser Ala Arg Ser
            980                 985                 990

Val Ser Pro Thr Thr Glu Met Val  Ser Asn Glu Ser Val  Asp Tyr Arg
        995                 1000                1005

Ala Thr Phe Pro Glu Asp Gln Phe Pro Asn Ser Ser  Gln Asn Gly
    1010                1015                1020

Ser Cys Arg Gln Val Gln Tyr Pro Leu Thr Asp Met  Ser Pro Ile
    1025                1030                1035

Leu Thr Ser Gly Asp Ser Asp Ile Ser Ser Pro Leu Leu Gln Asn
    1040                1045                1050

Thr Val His Ile Asp Leu Ser Ala Leu Asn Pro Glu Leu Val Gln
    1055                1060                1065

Ala Val Gln His Val Val Ile Gly Pro Ser Ser Leu Ile Val His
    1070                1075                1080

Phe Asn Glu Val Ile Gly Arg Gly His Phe Gly Cys Val Tyr His
    1085                1090                1095

Gly Thr Leu Leu Asp Asn Asp Gly Lys Lys Ile His Cys Ala Val
    1100                1105                1110

Lys Ser Leu Asn Arg Ile Thr Asp Ile Gly Glu Val Ser Gln Phe
    1115                1120                1125

Leu Thr Glu Gly Ile Ile Met Lys Asp Phe Ser His Pro Asn Val
    1130                1135                1140
```

Leu Ser Leu Leu Gly Ile Cys Leu Arg Ser Glu Gly Ser Pro Leu
    1145                1150                1155

Val Val Leu Pro Tyr Met Lys His Gly Asp Leu Arg Asn Phe Ile
    1160                1165                1170

Arg Asn Glu Thr His Asn Pro Thr Val Lys Asp Leu Ile Gly Phe
    1175                1180                1185

Gly Leu Gln Val Ala Lys Gly Met Lys Tyr Leu Ala Ser Lys Lys
    1190                1195                1200

Phe Val His Arg Asp Leu Ala Ala Arg Asn Cys Met Leu Asp Glu
    1205                1210                1215

Lys Phe Thr Val Lys Val Ala Asp Phe Gly Leu Ala Arg Asp Met
    1220                1225                1230

Tyr Asp Lys Glu Tyr Tyr Ser Val His Asn Lys Thr Gly Ala Lys
    1235                1240                1245

Leu Pro Val Lys Trp Met Ala Leu Glu Ser Leu Gln Thr Gln Lys
    1250                1255                1260

Phe Thr Thr Lys Ser Asp Val Trp Ser Phe Gly Val Leu Leu Trp
    1265                1270                1275

Glu Leu Met Thr Arg Gly Ala Pro Pro Tyr Pro Asp Val Asn Thr
    1280                1285                1290

Phe Asp Ile Thr Val Tyr Leu Leu Gln Gly Arg Arg Leu Leu Gln
    1295                1300                1305

Pro Glu Tyr Cys Pro Asp Pro Leu Tyr Glu Val Met Leu Lys Cys
    1310                1315                1320

Trp His Pro Lys Ala Glu Met Arg Pro Ser Phe Ser Glu Leu Val
    1325                1330                1335

Ser Arg Ile Ser Ala Ile Phe Ser Thr Phe Ile Gly Glu His Tyr
    1340                1345                1350

Val His Val Asn Ala Thr Tyr Val Asn Val Lys Cys Val Ala Pro
    1355                1360                1365

Tyr Pro Ser Leu Leu Ser Ser Glu Asp Asn Ala Asp Asp Glu Val
    1370                1375                1380

Asp Thr Arg Pro Ala Ser Phe Trp Glu Thr Ser
    1385                1390

<210> SEQ ID NO 2
<211> LENGTH: 20
<212> TYPE: PRT
<213> ORGANISM: human
<220> FEATURE:
<223> OTHER INFORMATION: Common PTPRZ1 portion of fusion proteins ZM

<400> SEQUENCE: 2

Met Arg Ile Leu Lys Arg Phe Leu Ala Cys Ile Gln Leu Leu Cys Val
1               5                   10                  15

Cys Arg Leu Asp
            20

<210> SEQ ID NO 3
<211> LENGTH: 1414
<212> TYPE: PRT
<213> ORGANISM: human
<220> FEATURE:
<223> OTHER INFORMATION: Fusion protein ZM1-2

<400> SEQUENCE: 3

```
Met Arg Ile Leu Lys Arg Phe Leu Ala Cys Ile Gln Leu Leu Cys Val
1               5                   10                  15

Cys Arg Leu Asp Lys Pro Leu Ile Met Lys Ala Pro Ala Val Leu Ala
            20                  25                  30

Pro Gly Ile Leu Val Leu Leu Phe Thr Leu Val Gln Arg Ser Asn Gly
        35                  40                  45

Glu Cys Lys Glu Ala Leu Ala Lys Ser Glu Met Asn Val Asn Met Lys
    50                  55                  60

Tyr Gln Leu Pro Asn Phe Thr Ala Glu Thr Pro Ile Gln Asn Val Ile
65                  70                  75                  80

Leu His Glu His His Ile Phe Leu Gly Ala Thr Asn Tyr Ile Tyr Val
                85                  90                  95

Leu Asn Glu Glu Asp Leu Gln Lys Val Ala Glu Tyr Lys Thr Gly Pro
            100                 105                 110

Val Leu Glu His Pro Asp Cys Phe Pro Cys Gln Asp Cys Ser Ser Lys
        115                 120                 125

Ala Asn Leu Ser Gly Gly Val Trp Lys Asp Asn Ile Asn Met Ala Leu
    130                 135                 140

Val Val Asp Thr Tyr Tyr Asp Asp Gln Leu Ile Ser Cys Gly Ser Val
145                 150                 155                 160

Asn Arg Gly Thr Cys Gln Arg His Val Phe Pro His Asn His Thr Ala
                165                 170                 175

Asp Ile Gln Ser Glu Val His Cys Ile Phe Ser Pro Gln Ile Glu Glu
            180                 185                 190

Pro Ser Gln Cys Pro Asp Cys Val Val Ser Ala Leu Gly Ala Lys Val
        195                 200                 205

Leu Ser Ser Val Lys Asp Arg Phe Ile Asn Phe Val Gly Asn Thr
    210                 215                 220

Ile Asn Ser Ser Tyr Phe Pro Asp His Pro Leu His Ser Ile Ser Val
225                 230                 235                 240

Arg Arg Leu Lys Glu Thr Lys Asp Gly Phe Met Phe Leu Thr Asp Gln
                245                 250                 255

Ser Tyr Ile Asp Val Leu Pro Glu Phe Arg Asp Ser Tyr Pro Ile Lys
            260                 265                 270

Tyr Val His Ala Phe Glu Ser Asn Asn Phe Ile Tyr Phe Leu Thr Val
        275                 280                 285

Gln Arg Glu Thr Leu Asp Ala Gln Thr Phe His Thr Arg Ile Ile Arg
    290                 295                 300

Phe Cys Ser Ile Asn Ser Gly Leu His Ser Tyr Met Glu Met Pro Leu
305                 310                 315                 320

Glu Cys Ile Leu Thr Glu Lys Arg Lys Lys Arg Ser Thr Lys Lys Glu
                325                 330                 335

Val Phe Asn Ile Leu Gln Ala Ala Tyr Val Ser Lys Pro Gly Ala Gln
            340                 345                 350

Leu Ala Arg Gln Ile Gly Ala Ser Leu Asn Asp Asp Ile Leu Phe Gly
        355                 360                 365

Val Phe Ala Gln Ser Lys Pro Asp Ser Ala Glu Pro Met Asp Arg Ser
    370                 375                 380

Ala Met Cys Ala Phe Pro Ile Lys Tyr Val Asn Asp Phe Phe Asn Lys
385                 390                 395                 400

Ile Val Asn Lys Asn Asn Val Arg Cys Leu Gln His Phe Tyr Gly Pro
                405                 410                 415
```

```
Asn His Glu His Cys Phe Asn Arg Thr Leu Leu Arg Asn Ser Ser Gly
                420                 425                 430

Cys Glu Ala Arg Arg Asp Glu Tyr Arg Thr Glu Phe Thr Ala Leu
            435                 440                 445

Gln Arg Val Asp Leu Phe Met Gly Gln Phe Ser Glu Val Leu Leu Thr
450                 455                 460

Ser Ile Ser Thr Phe Ile Lys Gly Asp Leu Thr Ile Ala Asn Leu Gly
465                 470                 475                 480

Thr Ser Glu Gly Arg Phe Met Gln Val Val Ser Arg Ser Gly Pro
            485                 490                 495

Ser Thr Pro His Val Asn Phe Leu Leu Asp Ser His Pro Val Ser Pro
            500                 505                 510

Glu Val Ile Val Glu His Thr Leu Asn Gln Asn Gly Tyr Thr Leu Val
            515                 520                 525

Ile Thr Gly Lys Lys Ile Thr Lys Ile Pro Leu Asn Gly Leu Gly Cys
    530                 535                 540

Arg His Phe Gln Ser Cys Ser Gln Cys Leu Ser Ala Pro Pro Phe Val
545                 550                 555                 560

Gln Cys Gly Trp Cys His Asp Lys Cys Val Arg Ser Glu Glu Cys Leu
                565                 570                 575

Ser Gly Thr Trp Thr Gln Gln Ile Cys Leu Pro Ala Ile Tyr Lys Val
            580                 585                 590

Phe Pro Asn Ser Ala Pro Leu Glu Gly Gly Thr Arg Leu Thr Ile Cys
        595                 600                 605

Gly Trp Asp Phe Gly Phe Arg Arg Asn Asn Lys Phe Asp Leu Lys Lys
    610                 615                 620

Thr Arg Val Leu Leu Gly Asn Glu Ser Cys Thr Leu Thr Leu Ser Glu
625                 630                 635                 640

Ser Thr Met Asn Thr Leu Lys Cys Thr Val Gly Pro Ala Met Asn Lys
                645                 650                 655

His Phe Asn Met Ser Ile Ile Ile Ser Asn Gly His Gly Thr Thr Gln
            660                 665                 670

Tyr Ser Thr Phe Ser Tyr Val Asp Pro Val Ile Thr Ser Ile Ser Pro
        675                 680                 685

Lys Tyr Gly Pro Met Ala Gly Gly Thr Leu Leu Thr Leu Thr Gly Asn
690                 695                 700

Tyr Leu Asn Ser Gly Asn Ser Arg His Ile Ser Ile Gly Gly Lys Thr
705                 710                 715                 720

Cys Thr Leu Lys Ser Val Ser Asn Ser Ile Leu Glu Cys Tyr Thr Pro
                725                 730                 735

Ala Gln Thr Ile Ser Thr Glu Phe Ala Val Lys Leu Lys Ile Asp Leu
            740                 745                 750

Ala Asn Arg Glu Thr Ser Ile Phe Ser Tyr Arg Glu Asp Pro Ile Val
            755                 760                 765

Tyr Glu Ile His Pro Thr Lys Ser Phe Ile Ser Gly Gly Ser Thr Ile
    770                 775                 780

Thr Gly Val Gly Lys Asn Leu Asn Ser Val Ser Val Pro Arg Met Val
785                 790                 795                 800

Ile Asn Val His Glu Ala Gly Arg Asn Phe Thr Val Ala Cys Gln His
            805                 810                 815

Arg Ser Asn Ser Glu Ile Ile Cys Cys Thr Thr Pro Ser Leu Gln Gln
            820                 825                 830
```

```
Leu Asn Leu Gln Leu Pro Leu Lys Thr Lys Ala Phe Phe Met Leu Asp
            835                 840                 845
Gly Ile Leu Ser Lys Tyr Phe Asp Leu Ile Tyr Val His Asn Pro Val
850                 855                 860
Phe Lys Pro Phe Glu Lys Pro Val Met Ile Ser Met Gly Asn Glu Asn
865                 870                 875                 880
Val Leu Glu Ile Lys Gly Asn Asp Ile Asp Pro Glu Ala Val Lys Gly
                885                 890                 895
Glu Val Leu Lys Val Gly Asn Lys Ser Cys Glu Asn Ile His Leu His
            900                 905                 910
Ser Glu Ala Val Leu Cys Thr Val Pro Asn Asp Leu Leu Lys Leu Asn
            915                 920                 925
Ser Glu Leu Asn Ile Glu Trp Lys Gln Ala Ile Ser Ser Thr Val Leu
            930                 935                 940
Gly Lys Val Ile Val Gln Pro Asp Gln Asn Phe Thr Gly Leu Ile Ala
945                 950                 955                 960
Gly Val Val Ser Ile Ser Thr Ala Leu Leu Leu Leu Gly Phe Phe
                965                 970                 975
Leu Trp Leu Lys Lys Arg Lys Gln Ile Lys Asp Leu Gly Ser Glu Leu
            980                 985                 990
Val Arg Tyr Asp Ala Arg Val His  Thr Pro His Leu Asp  Arg Leu Val
            995                 1000                1005
Ser Ala  Arg Ser Val Ser Pro  Thr Thr Glu Met Val  Ser Asn Glu
            1010                1015                1020
Ser Val  Asp Tyr Arg Ala Thr  Phe Pro Glu Asp Gln  Phe Pro Asn
            1025                1030                1035
Ser Ser  Gln Asn Gly Ser Cys  Arg Gln Val Gln Tyr  Pro Leu Thr
            1040                1045                1050
Asp Met  Ser Pro Ile Leu Thr  Ser Gly Asp Ser Asp  Ile Ser Ser
            1055                1060                1065
Pro Leu  Leu Gln Asn Thr Val  His Ile Asp Leu Ser  Ala Leu Asn
            1070                1075                1080
Pro Glu  Leu Val Gln Ala Val  Gln His Val Val Ile  Gly Pro Ser
            1085                1090                1095
Ser Leu  Ile Val His Phe Asn  Glu Val Ile Gly Arg  Gly His Phe
            1100                1105                1110
Gly Cys  Val Tyr His Gly Thr  Leu Leu Asp Asn Asp  Gly Lys Lys
            1115                1120                1125
Ile His  Cys Ala Val Lys Ser  Leu Asn Arg Ile Thr  Asp Ile Gly
            1130                1135                1140
Glu Val  Ser Gln Phe Leu Thr  Glu Gly Ile Ile Met  Lys Asp Phe
            1145                1150                1155
Ser His  Pro Asn Val Leu Ser  Leu Leu Gly Ile Cys  Leu Arg Ser
            1160                1165                1170
Glu Gly  Ser Pro Leu Val Val  Leu Pro Tyr Met Lys  His Gly Asp
            1175                1180                1185
Leu Arg  Asn Phe Ile Arg Asn  Glu Thr His Asn Pro  Thr Val Lys
            1190                1195                1200
Asp Leu  Ile Gly Phe Gly Leu  Gln Val Ala Lys Gly  Met Lys Tyr
            1205                1210                1215
Leu Ala  Ser Lys Lys Phe Val  His Arg Asp Leu Ala  Ala Arg Asn
            1220                1225                1230
```

-continued

```
Cys Met Leu Asp Glu Lys Phe Thr Val Lys Val Ala Asp Phe Gly
    1235                1240                1245

Leu Ala Arg Asp Met Tyr Asp Lys Glu Tyr Tyr Ser Val His Asn
    1250                1255                1260

Lys Thr Gly Ala Lys Leu Pro Val Lys Trp Met Ala Leu Glu Ser
    1265                1270                1275

Leu Gln Thr Gln Lys Phe Thr Thr Lys Ser Asp Val Trp Ser Phe
    1280                1285                1290

Gly Val Leu Leu Trp Glu Leu Met Thr Arg Gly Ala Pro Pro Tyr
    1295                1300                1305

Pro Asp Val Asn Thr Phe Asp Ile Thr Val Tyr Leu Leu Gln Gly
    1310                1315                1320

Arg Arg Leu Leu Gln Pro Glu Tyr Cys Pro Asp Pro Leu Tyr Glu
    1325                1330                1335

Val Met Leu Lys Cys Trp His Pro Lys Ala Glu Met Arg Pro Ser
    1340                1345                1350

Phe Ser Glu Leu Val Ser Arg Ile Ser Ala Ile Phe Ser Thr Phe
    1355                1360                1365

Ile Gly Glu His Tyr Val His Val Asn Ala Thr Tyr Val Asn Val
    1370                1375                1380

Lys Cys Val Ala Pro Tyr Pro Ser Leu Leu Ser Ser Glu Asp Asn
    1385                1390                1395

Ala Asp Asp Glu Val Asp Thr Arg Pro Ala Ser Phe Trp Glu Thr
    1400                1405                1410

Ser
```

<210> SEQ ID NO 4
<211> LENGTH: 1436
<212> TYPE: PRT
<213> ORGANISM: human
<220> FEATURE:
<223> OTHER INFORMATION: Fusion protein ZM2-2

<400> SEQUENCE: 4

```
Met Arg Ile Leu Lys Arg Phe Leu Ala Cys Ile Gln Leu Leu Cys Val
1               5                   10                  15

Cys Arg Leu Asp Trp Ala Asn Gly Tyr Tyr Arg Gln Gln Arg Lys Leu
            20                  25                  30

Val Glu Glu Ile Gly Trp Ser Tyr Thr Asp Lys Pro Leu Ile Met Lys
        35                  40                  45

Ala Pro Ala Val Leu Ala Pro Gly Ile Leu Val Leu Leu Phe Thr Leu
    50                  55                  60

Val Gln Arg Ser Asn Gly Glu Cys Lys Glu Ala Leu Ala Lys Ser Glu
65                  70                  75                  80

Met Asn Val Asn Met Lys Tyr Gln Leu Pro Asn Phe Thr Ala Glu Thr
                85                  90                  95

Pro Ile Gln Asn Val Ile Leu His Glu His His Ile Phe Leu Gly Ala
            100                 105                 110

Thr Asn Tyr Ile Tyr Val Leu Asn Glu Glu Asp Leu Gln Lys Val Ala
        115                 120                 125

Glu Tyr Lys Thr Gly Pro Val Leu Glu His Pro Asp Cys Phe Pro Cys
    130                 135                 140

Gln Asp Cys Ser Ser Lys Ala Asn Leu Ser Gly Gly Val Trp Lys Asp
145                 150                 155                 160
```

```
Asn Ile Asn Met Ala Leu Val Val Asp Thr Tyr Tyr Asp Asp Gln Leu
            165                 170                 175

Ile Ser Cys Gly Ser Val Asn Arg Gly Thr Cys Gln Arg His Val Phe
        180                 185                 190

Pro His Asn His Thr Ala Asp Ile Gln Ser Glu Val His Cys Ile Phe
        195                 200                 205

Ser Pro Gln Ile Glu Glu Pro Ser Gln Cys Pro Asp Cys Val Val Ser
    210                 215                 220

Ala Leu Gly Ala Lys Val Leu Ser Ser Val Lys Asp Arg Phe Ile Asn
225                 230                 235                 240

Phe Phe Val Gly Asn Thr Ile Asn Ser Ser Tyr Phe Pro Asp His Pro
                245                 250                 255

Leu His Ser Ile Ser Val Arg Arg Leu Lys Glu Thr Lys Asp Gly Phe
            260                 265                 270

Met Phe Leu Thr Asp Gln Ser Tyr Ile Asp Val Leu Pro Glu Phe Arg
        275                 280                 285

Asp Ser Tyr Pro Ile Lys Tyr Val His Ala Phe Glu Ser Asn Asn Phe
    290                 295                 300

Ile Tyr Phe Leu Thr Val Gln Arg Glu Thr Leu Asp Ala Gln Thr Phe
305                 310                 315                 320

His Thr Arg Ile Ile Arg Phe Cys Ser Ile Asn Ser Gly Leu His Ser
                325                 330                 335

Tyr Met Glu Met Pro Leu Glu Cys Ile Leu Thr Glu Lys Arg Lys Lys
            340                 345                 350

Arg Ser Thr Lys Lys Glu Val Phe Asn Ile Leu Gln Ala Ala Tyr Val
        355                 360                 365

Ser Lys Pro Gly Ala Gln Leu Ala Arg Gln Ile Gly Ala Ser Leu Asn
    370                 375                 380

Asp Asp Ile Leu Phe Gly Val Phe Ala Gln Ser Lys Pro Asp Ser Ala
385                 390                 395                 400

Glu Pro Met Asp Arg Ser Ala Met Cys Ala Phe Pro Ile Lys Tyr Val
                405                 410                 415

Asn Asp Phe Phe Asn Lys Ile Val Asn Lys Asn Asn Val Arg Cys Leu
            420                 425                 430

Gln His Phe Tyr Gly Pro Asn His Glu His Cys Phe Asn Arg Thr Leu
        435                 440                 445

Leu Arg Asn Ser Ser Gly Cys Glu Ala Arg Arg Asp Glu Tyr Arg Thr
    450                 455                 460

Glu Phe Thr Thr Ala Leu Gln Arg Val Asp Leu Phe Met Gly Gln Phe
465                 470                 475                 480

Ser Glu Val Leu Leu Thr Ser Ile Ser Thr Phe Ile Lys Gly Asp Leu
                485                 490                 495

Thr Ile Ala Asn Leu Gly Thr Ser Glu Gly Arg Phe Met Gln Val Val
            500                 505                 510

Val Ser Arg Ser Gly Pro Ser Thr Pro His Val Asn Phe Leu Leu Asp
        515                 520                 525

Ser His Pro Val Ser Pro Glu Val Ile Val His Thr Leu Asn Gln
    530                 535                 540

Asn Gly Tyr Thr Leu Val Ile Thr Gly Lys Lys Ile Thr Lys Ile Pro
545                 550                 555                 560

Leu Asn Gly Leu Gly Cys Arg His Phe Gln Ser Cys Ser Gln Cys Leu
                565                 570                 575
```

-continued

Ser Ala Pro Pro Phe Val Gln Cys Gly Trp Cys His Asp Lys Cys Val
            580                 585                 590

Arg Ser Glu Glu Cys Leu Ser Gly Thr Trp Thr Gln Gln Ile Cys Leu
        595                 600                 605

Pro Ala Ile Tyr Lys Val Phe Pro Asn Ser Ala Pro Leu Glu Gly Gly
        610                 615                 620

Thr Arg Leu Thr Ile Cys Gly Trp Asp Phe Gly Phe Arg Arg Asn Asn
625                 630                 635                 640

Lys Phe Asp Leu Lys Lys Thr Arg Val Leu Leu Gly Asn Glu Ser Cys
            645                 650                 655

Thr Leu Thr Leu Ser Glu Ser Thr Met Asn Thr Leu Lys Cys Thr Val
            660                 665                 670

Gly Pro Ala Met Asn Lys His Phe Asn Met Ser Ile Ile Ile Ser Asn
            675                 680                 685

Gly His Gly Thr Thr Gln Tyr Ser Thr Phe Ser Tyr Val Asp Pro Val
            690                 695                 700

Ile Thr Ser Ile Ser Pro Lys Tyr Gly Pro Met Ala Gly Gly Thr Leu
705                 710                 715                 720

Leu Thr Leu Thr Gly Asn Tyr Leu Asn Ser Gly Asn Ser Arg His Ile
                725                 730                 735

Ser Ile Gly Gly Lys Thr Cys Thr Leu Lys Ser Val Ser Asn Ser Ile
            740                 745                 750

Leu Glu Cys Tyr Thr Pro Ala Gln Thr Ile Ser Thr Glu Phe Ala Val
            755                 760                 765

Lys Leu Lys Ile Asp Leu Ala Asn Arg Glu Thr Ser Ile Phe Ser Tyr
            770                 775                 780

Arg Glu Asp Pro Ile Val Tyr Glu Ile His Pro Thr Lys Ser Phe Ile
785                 790                 795                 800

Ser Gly Gly Ser Thr Ile Thr Gly Val Gly Lys Asn Leu Asn Ser Val
                805                 810                 815

Ser Val Pro Arg Met Val Ile Asn Val His Glu Ala Gly Arg Asn Phe
            820                 825                 830

Thr Val Ala Cys Gln His Arg Ser Asn Ser Glu Ile Ile Cys Cys Thr
            835                 840                 845

Thr Pro Ser Leu Gln Gln Leu Asn Leu Gln Leu Pro Leu Lys Thr Lys
850                 855                 860

Ala Phe Phe Met Leu Asp Gly Ile Leu Ser Lys Tyr Phe Asp Leu Ile
865                 870                 875                 880

Tyr Val His Asn Pro Val Phe Lys Pro Phe Glu Lys Pro Val Met Ile
                885                 890                 895

Ser Met Gly Asn Glu Asn Val Leu Glu Ile Lys Gly Asn Asp Ile Asp
            900                 905                 910

Pro Glu Ala Val Lys Gly Glu Val Leu Lys Val Gly Asn Lys Ser Cys
            915                 920                 925

Glu Asn Ile His Leu His Ser Glu Ala Val Leu Cys Thr Val Pro Asn
            930                 935                 940

Asp Leu Leu Lys Leu Asn Ser Glu Leu Asn Ile Glu Trp Lys Gln Ala
945                 950                 955                 960

Ile Ser Ser Thr Val Leu Gly Lys Val Ile Val Gln Pro Asp Gln Asn
                965                 970                 975

Phe Thr Gly Leu Ile Ala Gly Val Val Ser Ile Ser Thr Ala Leu Leu
            980                 985                 990

-continued

Leu Leu Leu Gly Phe Phe Leu Trp Leu Lys Lys Arg Lys Gln Ile Lys
            995                 1000                1005

Asp Leu Gly Ser Glu Leu Val Arg Tyr Asp Ala Arg Val His Thr
    1010                1015                1020

Pro His Leu Asp Arg Leu Val Ser Ala Arg Ser Val Ser Pro Thr
    1025                1030                1035

Thr Glu Met Val Ser Asn Glu Ser Val Asp Tyr Arg Ala Thr Phe
    1040                1045                1050

Pro Glu Asp Gln Phe Pro Asn Ser Ser Gln Asn Gly Ser Cys Arg
    1055                1060                1065

Gln Val Gln Tyr Pro Leu Thr Asp Met Ser Pro Ile Leu Thr Ser
    1070                1075                1080

Gly Asp Ser Asp Ile Ser Ser Pro Leu Leu Gln Asn Thr Val His
    1085                1090                1095

Ile Asp Leu Ser Ala Leu Asn Pro Glu Leu Val Gln Ala Val Gln
    1100                1105                1110

His Val Val Ile Gly Pro Ser Ser Leu Ile Val His Phe Asn Glu
    1115                1120                1125

Val Ile Gly Arg Gly His Phe Gly Cys Val Tyr His Gly Thr Leu
    1130                1135                1140

Leu Asp Asn Asp Gly Lys Lys Ile His Cys Ala Val Lys Ser Leu
    1145                1150                1155

Asn Arg Ile Thr Asp Ile Gly Glu Val Ser Gln Phe Leu Thr Glu
    1160                1165                1170

Gly Ile Ile Met Lys Asp Phe Ser His Pro Asn Val Leu Ser Leu
    1175                1180                1185

Leu Gly Ile Cys Leu Arg Ser Glu Gly Ser Pro Leu Val Val Leu
    1190                1195                1200

Pro Tyr Met Lys His Gly Asp Leu Arg Asn Phe Ile Arg Asn Glu
    1205                1210                1215

Thr His Asn Pro Thr Val Lys Asp Leu Ile Gly Phe Gly Leu Gln
    1220                1225                1230

Val Ala Lys Gly Met Lys Tyr Leu Ala Ser Lys Lys Phe Val His
    1235                1240                1245

Arg Asp Leu Ala Ala Arg Asn Cys Met Leu Asp Glu Lys Phe Thr
    1250                1255                1260

Val Lys Val Ala Asp Phe Gly Leu Ala Arg Asp Met Tyr Asp Lys
    1265                1270                1275

Glu Tyr Tyr Ser Val His Asn Lys Thr Gly Ala Lys Leu Pro Val
    1280                1285                1290

Lys Trp Met Ala Leu Glu Ser Leu Gln Thr Gln Lys Phe Thr Thr
    1295                1300                1305

Lys Ser Asp Val Trp Ser Phe Gly Val Leu Leu Trp Glu Leu Met
    1310                1315                1320

Thr Arg Gly Ala Pro Pro Tyr Pro Asp Val Asn Thr Phe Asp Ile
    1325                1330                1335

Thr Val Tyr Leu Leu Gln Gly Arg Arg Leu Leu Gln Pro Glu Tyr
    1340                1345                1350

Cys Pro Asp Pro Leu Tyr Glu Val Met Leu Lys Cys Trp His Pro
    1355                1360                1365

Lys Ala Glu Met Arg Pro Ser Phe Ser Glu Leu Val Ser Arg Ile
    1370                1375                1380

```
Ser Ala Ile Phe Ser Thr Phe Ile Gly Glu His Tyr Val His Val
    1385            1390                1395

Asn Ala Thr Tyr Val Asn Val Lys Cys Val Ala Pro Tyr Pro Ser
1400                1405                1410

Leu Leu Ser Ser Glu Asp Asn Ala Asp Asp Val Asp Thr Arg
    1415            1420                1425

Pro Ala Ser Phe Trp Glu Thr Ser
1430                1435

<210> SEQ ID NO 5
<211> LENGTH: 1496
<212> TYPE: PRT
<213> ORGANISM: human
<220> FEATURE:
<223> OTHER INFORMATION: Fusion protein ZM3-2

<400> SEQUENCE: 5

Met Arg Ile Leu Lys Arg Phe Leu Ala Cys Ile Gln Leu Leu Cys Val
1               5                   10                  15

Cys Arg Leu Asp Trp Ala Asn Gly Tyr Tyr Arg Gln Arg Lys Leu
            20                  25                  30

Val Glu Glu Ile Gly Trp Ser Tyr Thr Gly Ala Leu Asn Gln Lys Asn
        35                  40                  45

Trp Gly Lys Lys Tyr Pro Thr Cys Asn Ser Pro Lys Gln Ser Pro Ile
    50                  55                  60

Asn Ile Asp Glu Asp Leu Thr Gln Val Asn Val Asn Leu Lys Lys Leu
65                  70                  75                  80

Lys Phe Gln Gly Trp Asp Lys Thr Ser Leu Glu Asn Thr Phe Ile His
                85                  90                  95

Asn Thr Gly Lys Thr Asp Lys Pro Leu Ile Met Lys Ala Pro Ala Val
            100                 105                 110

Leu Ala Pro Gly Ile Leu Val Leu Leu Phe Thr Leu Val Gln Arg Ser
        115                 120                 125

Asn Gly Glu Cys Lys Glu Ala Leu Ala Lys Ser Glu Met Asn Val Asn
    130                 135                 140

Met Lys Tyr Gln Leu Pro Asn Phe Thr Ala Glu Thr Pro Ile Gln Asn
145                 150                 155                 160

Val Ile Leu His Glu His His Ile Phe Leu Gly Ala Thr Asn Tyr Ile
                165                 170                 175

Tyr Val Leu Asn Glu Glu Asp Leu Gln Lys Val Ala Glu Tyr Lys Thr
            180                 185                 190

Gly Pro Val Leu Glu His Pro Asp Cys Phe Pro Cys Gln Asp Cys Ser
        195                 200                 205

Ser Lys Ala Asn Leu Ser Gly Gly Val Trp Lys Asp Asn Ile Asn Met
    210                 215                 220

Ala Leu Val Val Asp Thr Tyr Tyr Asp Asp Gln Leu Ile Ser Cys Gly
225                 230                 235                 240

Ser Val Asn Arg Gly Thr Cys Gln Arg His Val Phe Pro His Asn His
                245                 250                 255

Thr Ala Asp Ile Gln Ser Glu Val His Cys Ile Phe Ser Pro Gln Ile
            260                 265                 270

Glu Glu Pro Ser Gln Cys Pro Asp Cys Val Val Ser Ala Leu Gly Ala
        275                 280                 285

Lys Val Leu Ser Ser Val Lys Asp Arg Phe Ile Asn Phe Phe Val Gly
    290                 295                 300
```

-continued

```
Asn Thr Ile Asn Ser Ser Tyr Phe Pro Asp His Pro Leu His Ser Ile
305                 310                 315                 320

Ser Val Arg Arg Leu Lys Glu Thr Lys Asp Gly Phe Met Phe Leu Thr
            325                 330                 335

Asp Gln Ser Tyr Ile Asp Val Leu Pro Glu Phe Arg Asp Ser Tyr Pro
            340                 345                 350

Ile Lys Tyr Val His Ala Phe Glu Ser Asn Asn Phe Ile Tyr Phe Leu
            355                 360                 365

Thr Val Gln Arg Glu Thr Leu Asp Ala Gln Thr Phe His Thr Arg Ile
370                 375                 380

Ile Arg Phe Cys Ser Ile Asn Ser Gly Leu His Ser Tyr Met Glu Met
385                 390                 395                 400

Pro Leu Glu Cys Ile Leu Thr Glu Lys Arg Lys Lys Arg Ser Thr Lys
                405                 410                 415

Lys Glu Val Phe Asn Ile Leu Gln Ala Ala Tyr Val Ser Lys Pro Gly
            420                 425                 430

Ala Gln Leu Ala Arg Gln Ile Gly Ala Ser Leu Asn Asp Asp Ile Leu
            435                 440                 445

Phe Gly Val Phe Ala Gln Ser Lys Pro Asp Ser Ala Glu Pro Met Asp
450                 455                 460

Arg Ser Ala Met Cys Ala Phe Pro Ile Lys Tyr Val Asn Asp Phe Phe
465                 470                 475                 480

Asn Lys Ile Val Asn Lys Asn Val Arg Cys Leu Gln His Phe Tyr
                485                 490                 495

Gly Pro Asn His Glu His Cys Phe Asn Arg Thr Leu Leu Arg Asn Ser
                500                 505                 510

Ser Gly Cys Glu Ala Arg Arg Asp Glu Tyr Arg Thr Glu Phe Thr Thr
            515                 520                 525

Ala Leu Gln Arg Val Asp Leu Phe Met Gly Gln Phe Ser Glu Val Leu
            530                 535                 540

Leu Thr Ser Ile Ser Thr Phe Ile Lys Gly Asp Leu Thr Ile Ala Asn
545                 550                 555                 560

Leu Gly Thr Ser Glu Gly Arg Phe Met Gln Val Val Ser Arg Ser
                565                 570                 575

Gly Pro Ser Thr Pro His Val Asn Phe Leu Leu Asp Ser His Pro Val
            580                 585                 590

Ser Pro Glu Val Ile Val Glu His Thr Leu Asn Gln Asn Gly Tyr Thr
            595                 600                 605

Leu Val Ile Thr Gly Lys Lys Ile Thr Lys Ile Pro Leu Asn Gly Leu
610                 615                 620

Gly Cys Arg His Phe Gln Ser Cys Ser Gln Cys Leu Ser Ala Pro Pro
625                 630                 635                 640

Phe Val Gln Cys Gly Trp Cys His Asp Lys Cys Val Arg Ser Glu Glu
                645                 650                 655

Cys Leu Ser Gly Thr Trp Thr Gln Gln Ile Cys Leu Pro Ala Ile Tyr
            660                 665                 670

Lys Val Phe Pro Asn Ser Ala Pro Leu Glu Gly Gly Thr Arg Leu Thr
            675                 680                 685

Ile Cys Gly Trp Asp Phe Gly Phe Arg Arg Asn Asn Lys Phe Asp Leu
            690                 695                 700

Lys Lys Thr Arg Val Leu Leu Gly Asn Glu Ser Cys Thr Leu Thr Leu
705                 710                 715                 720
```

```
Ser Glu Ser Thr Met Asn Thr Leu Lys Cys Thr Val Gly Pro Ala Met
                725                 730                 735

Asn Lys His Phe Asn Met Ser Ile Ile Ile Ser Asn Gly His Gly Thr
            740                 745                 750

Thr Gln Tyr Ser Thr Phe Ser Tyr Val Asp Pro Val Ile Thr Ser Ile
        755                 760                 765

Ser Pro Lys Tyr Gly Pro Met Ala Gly Gly Thr Leu Leu Thr Leu Thr
770                 775                 780

Gly Asn Tyr Leu Asn Ser Gly Asn Ser Arg His Ile Ser Ile Gly Gly
785                 790                 795                 800

Lys Thr Cys Thr Leu Lys Ser Val Ser Asn Ser Ile Leu Glu Cys Tyr
                805                 810                 815

Thr Pro Ala Gln Thr Ile Ser Thr Glu Phe Ala Val Lys Leu Lys Ile
            820                 825                 830

Asp Leu Ala Asn Arg Glu Thr Ser Ile Phe Ser Tyr Arg Glu Asp Pro
        835                 840                 845

Ile Val Tyr Glu Ile His Pro Thr Lys Ser Phe Ile Ser Gly Gly Ser
    850                 855                 860

Thr Ile Thr Gly Val Gly Lys Asn Leu Asn Ser Val Ser Val Pro Arg
865                 870                 875                 880

Met Val Ile Asn Val His Glu Ala Gly Arg Asn Phe Thr Val Ala Cys
                885                 890                 895

Gln His Arg Ser Asn Ser Glu Ile Ile Cys Cys Thr Thr Pro Ser Leu
            900                 905                 910

Gln Gln Leu Asn Leu Gln Leu Pro Leu Lys Thr Lys Ala Phe Phe Met
        915                 920                 925

Leu Asp Gly Ile Leu Ser Lys Tyr Phe Asp Leu Ile Tyr Val His Asn
    930                 935                 940

Pro Val Phe Lys Pro Phe Glu Lys Pro Val Met Ile Ser Met Gly Asn
945                 950                 955                 960

Glu Asn Val Leu Glu Ile Lys Gly Asn Asp Ile Asp Pro Glu Ala Val
                965                 970                 975

Lys Gly Glu Val Leu Lys Val Gly Asn Lys Ser Cys Glu Asn Ile His
            980                 985                 990

Leu His Ser Glu Ala Val Leu Cys Thr Val Pro Asn Asp Leu Leu Lys
        995                 1000                1005

Leu Asn Ser Glu Leu Asn Ile Glu Trp Lys Gln Ala Ile Ser Ser
    1010                1015                1020

Thr Val Leu Gly Lys Val Ile Val Gln Pro Asp Gln Asn Phe Thr
    1025                1030                1035

Gly Leu Ile Ala Gly Val Val Ser Ile Ser Thr Ala Leu Leu Leu
    1040                1045                1050

Leu Leu Gly Phe Phe Leu Trp Leu Lys Lys Arg Lys Gln Ile Lys
    1055                1060                1065

Asp Leu Gly Ser Glu Leu Val Arg Tyr Asp Ala Arg Val His Thr
    1070                1075                1080

Pro His Leu Asp Arg Leu Val Ser Ala Arg Ser Val Ser Pro Thr
    1085                1090                1095

Thr Glu Met Val Ser Asn Glu Ser Val Asp Tyr Arg Ala Thr Phe
    1100                1105                1110

Pro Glu Asp Gln Phe Pro Asn Ser Ser Gln Asn Gly Ser Cys Arg
    1115                1120                1125
```

-continued

| | | | | | | | | | | | |
|---|---|---|---|---|---|---|---|---|---|---|---|
|Gln|Val|Gln|Tyr|Pro|Leu|Thr|Asp|Met|Ser|Pro|Ile|Leu|Thr|Ser|
| |1130| | | |1135| | | |1140| | | | | |

Gln Val Gln Tyr Pro Leu Thr Asp Met Ser Pro Ile Leu Thr Ser
　　 1130　　　　　　　　1135　　　　　　　　1140

Gly Asp Ser Asp Ile Ser Ser Pro Leu Leu Gln Asn Thr Val His
　　 1145　　　　　　　　1150　　　　　　　　1155

Ile Asp Leu Ser Ala Leu Asn Pro Glu Leu Val Gln Ala Val Gln
　　 1160　　　　　　　　1165　　　　　　　　1170

His Val Val Ile Gly Pro Ser Ser Leu Ile Val His Phe Asn Glu
　　 1175　　　　　　　　1180　　　　　　　　1185

Val Ile Gly Arg Gly His Phe Gly Cys Val Tyr His Gly Thr Leu
　　 1190　　　　　　　　1195　　　　　　　　1200

Leu Asp Asn Asp Gly Lys Lys Ile His Cys Ala Val Lys Ser Leu
　　 1205　　　　　　　　1210　　　　　　　　1215

Asn Arg Ile Thr Asp Ile Gly Glu Val Ser Gln Phe Leu Thr Glu
　　 1220　　　　　　　　1225　　　　　　　　1230

Gly Ile Ile Met Lys Asp Phe Ser His Pro Asn Val Leu Ser Leu
　　 1235　　　　　　　　1240　　　　　　　　1245

Leu Gly Ile Cys Leu Arg Ser Glu Gly Ser Pro Leu Val Val Leu
　　 1250　　　　　　　　1255　　　　　　　　1260

Pro Tyr Met Lys His Gly Asp Leu Arg Asn Phe Ile Arg Asn Glu
　　 1265　　　　　　　　1270　　　　　　　　1275

Thr His Asn Pro Thr Val Lys Asp Leu Ile Gly Phe Gly Leu Gln
　　 1280　　　　　　　　1285　　　　　　　　1290

Val Ala Lys Gly Met Lys Tyr Leu Ala Ser Lys Lys Phe Val His
　　 1295　　　　　　　　1300　　　　　　　　1305

Arg Asp Leu Ala Ala Arg Asn Cys Met Leu Asp Glu Lys Phe Thr
　　 1310　　　　　　　　1315　　　　　　　　1320

Val Lys Val Ala Asp Phe Gly Leu Ala Arg Asp Met Tyr Asp Lys
　　 1325　　　　　　　　1330　　　　　　　　1335

Glu Tyr Tyr Ser Val His Asn Lys Thr Gly Ala Lys Leu Pro Val
　　 1340　　　　　　　　1345　　　　　　　　1350

Lys Trp Met Ala Leu Glu Ser Leu Gln Thr Gln Lys Phe Thr Thr
　　 1355　　　　　　　　1360　　　　　　　　1365

Lys Ser Asp Val Trp Ser Phe Gly Val Leu Leu Trp Glu Leu Met
　　 1370　　　　　　　　1375　　　　　　　　1380

Thr Arg Gly Ala Pro Pro Tyr Pro Asp Val Asn Thr Phe Asp Ile
　　 1385　　　　　　　　1390　　　　　　　　1395

Thr Val Tyr Leu Leu Gln Gly Arg Arg Leu Leu Gln Pro Glu Tyr
　　 1400　　　　　　　　1405　　　　　　　　1410

Cys Pro Asp Pro Leu Tyr Glu Val Met Leu Lys Cys Trp His Pro
　　 1415　　　　　　　　1420　　　　　　　　1425

Lys Ala Glu Met Arg Pro Ser Phe Ser Glu Leu Val Ser Arg Ile
　　 1430　　　　　　　　1435　　　　　　　　1440

Ser Ala Ile Phe Ser Thr Phe Ile Gly Glu His Tyr Val His Val
　　 1445　　　　　　　　1450　　　　　　　　1455

Asn Ala Thr Tyr Val Asn Val Lys Cys Val Ala Pro Tyr Pro Ser
　　 1460　　　　　　　　1465　　　　　　　　1470

Leu Leu Ser Ser Glu Asp Asn Ala Asp Asp Glu Val Asp Thr Arg
　　 1475　　　　　　　　1480　　　　　　　　1485

Pro Ala Ser Phe Trp Glu Thr Ser
　　 1490　　　　　　　　1495

```
<210> SEQ ID NO 6
<211> LENGTH: 1704
<212> TYPE: PRT
<213> ORGANISM: human
<220> FEATURE:
<223> OTHER INFORMATION: Fusion protein ZM8-2

<400> SEQUENCE: 6
```

| | | | | | | | | | | | | | | | |
|---|---|---|---|---|---|---|---|---|---|---|---|---|---|---|---|
| Met | Arg | Ile | Leu | Lys | Arg | Phe | Leu | Ala | Cys | Ile | Gln | Leu | Leu | Cys | Val |
| 1 | | | | 5 | | | | | 10 | | | | | 15 | |
| Cys | Arg | Leu | Asp | Trp | Ala | Asn | Gly | Tyr | Tyr | Arg | Gln | Arg | Lys | Leu | |
| | | | 20 | | | | | 25 | | | | | 30 | | |
| Val | Glu | Glu | Ile | Gly | Trp | Ser | Tyr | Thr | Gly | Ala | Leu | Asn | Gln | Lys | Asn |
| | | | 35 | | | | | 40 | | | | | 45 | | |
| Trp | Gly | Lys | Lys | Tyr | Pro | Thr | Cys | Asn | Ser | Pro | Lys | Gln | Ser | Pro | Ile |
| 50 | | | | | | 55 | | | | | 60 | | | | |
| Asn | Ile | Asp | Glu | Asp | Leu | Thr | Gln | Val | Asn | Val | Asn | Leu | Lys | Lys | Leu |
| 65 | | | | | 70 | | | | | 75 | | | | | 80 |
| Lys | Phe | Gln | Gly | Trp | Asp | Lys | Thr | Ser | Leu | Glu | Asn | Thr | Phe | Ile | His |
| | | | | 85 | | | | | 90 | | | | | 95 | |
| Asn | Thr | Gly | Lys | Thr | Val | Glu | Ile | Asn | Leu | Thr | Asn | Asp | Tyr | Arg | Val |
| | | | 100 | | | | | 105 | | | | | 110 | | |
| Ser | Gly | Gly | Val | Ser | Glu | Met | Val | Phe | Lys | Ala | Ser | Lys | Ile | Thr | Phe |
| | | | 115 | | | | | 120 | | | | | 125 | | |
| His | Trp | Gly | Lys | Cys | Asn | Met | Ser | Ser | Asp | Gly | Ser | Glu | His | Ser | Leu |
| | | | 130 | | | | | 135 | | | | | 140 | | |
| Glu | Gly | Gln | Lys | Phe | Pro | Leu | Glu | Met | Gln | Ile | Tyr | Cys | Phe | Asp | Ala |
| 145 | | | | | | 150 | | | | | 155 | | | | 160 |
| Asp | Arg | Phe | Ser | Ser | Phe | Glu | Glu | Ala | Val | Lys | Gly | Lys | Gly | Lys | Leu |
| | | | | 165 | | | | | 170 | | | | | 175 | |
| Arg | Ala | Leu | Ser | Ile | Leu | Phe | Glu | Val | Gly | Thr | Glu | Glu | Asn | Leu | Asp |
| | | | 180 | | | | | 185 | | | | | 190 | | |
| Phe | Lys | Ala | Ile | Ile | Asp | Gly | Val | Glu | Ser | Val | Ser | Arg | Phe | Gly | Lys |
| | | | 195 | | | | | 200 | | | | | 205 | | |
| Gln | Ala | Ala | Leu | Asp | Pro | Phe | Ile | Leu | Leu | Asn | Leu | Leu | Pro | Asn | Ser |
| | | | 210 | | | | | 215 | | | | | 220 | | |
| Thr | Asp | Lys | Tyr | Tyr | Ile | Tyr | Asn | Gly | Ser | Leu | Thr | Ser | Pro | Pro | Cys |
| 225 | | | | | | 230 | | | | | 235 | | | | 240 |
| Thr | Asp | Thr | Val | Asp | Trp | Ile | Val | Phe | Lys | Asp | Thr | Val | Ser | Ile | Ser |
| | | | | 245 | | | | | 250 | | | | | 255 | |
| Glu | Ser | Gln | Leu | Ala | Val | Phe | Cys | Glu | Val | Leu | Thr | Met | Gln | Gln | Ser |
| | | | 260 | | | | | 265 | | | | | 270 | | |
| Gly | Tyr | Val | Met | Leu | Met | Asp | Tyr | Leu | Gln | Asn | Asn | Phe | Arg | Glu | Gln |
| | | | 275 | | | | | 280 | | | | | 285 | | |
| Gln | Tyr | Lys | Phe | Ser | Arg | Gln | Val | Phe | Ser | Ser | Tyr | Thr | Gly | Lys | Glu |
| | | | 290 | | | | | 295 | | | | | 300 | | |
| Glu | Ile | His | Glu | Ala | Asp | Lys | Pro | Leu | Ile | Met | Lys | Ala | Pro | Ala | Val |
| 305 | | | | | | 310 | | | | | 315 | | | | 320 |
| Leu | Ala | Pro | Gly | Ile | Leu | Val | Leu | Leu | Phe | Thr | Leu | Val | Gln | Arg | Ser |
| | | | | 325 | | | | | 330 | | | | | 335 | |
| Asn | Gly | Glu | Cys | Lys | Glu | Ala | Leu | Ala | Lys | Ser | Glu | Met | Asn | Val | Asn |
| | | | 340 | | | | | 345 | | | | | 350 | | |
| Met | Lys | Tyr | Gln | Leu | Pro | Asn | Phe | Thr | Ala | Glu | Thr | Pro | Ile | Gln | Asn |
| | | | 355 | | | | | 360 | | | | | 365 | | |

-continued

```
Val Ile Leu His Glu His His Ile Phe Leu Gly Ala Thr Asn Tyr Ile
370                 375                 380

Tyr Val Leu Asn Glu Glu Asp Leu Gln Lys Val Ala Glu Tyr Lys Thr
385                 390                 395                 400

Gly Pro Val Leu Glu His Pro Asp Cys Phe Pro Cys Gln Asp Cys Ser
            405                 410                 415

Ser Lys Ala Asn Leu Ser Gly Gly Val Trp Lys Asp Asn Ile Asn Met
            420                 425                 430

Ala Leu Val Val Asp Thr Tyr Tyr Asp Asp Gln Leu Ile Ser Cys Gly
            435                 440                 445

Ser Val Asn Arg Gly Thr Cys Gln Arg His Val Phe Pro His Asn His
450                 455                 460

Thr Ala Asp Ile Gln Ser Glu Val His Cys Ile Phe Ser Pro Gln Ile
465                 470                 475                 480

Glu Glu Pro Ser Gln Cys Pro Asp Cys Val Val Ser Ala Leu Gly Ala
            485                 490                 495

Lys Val Leu Ser Ser Val Lys Asp Arg Phe Ile Asn Phe Phe Val Gly
            500                 505                 510

Asn Thr Ile Asn Ser Ser Tyr Phe Pro Asp His Pro Leu His Ser Ile
            515                 520                 525

Ser Val Arg Arg Leu Lys Glu Thr Lys Asp Gly Phe Met Phe Leu Thr
530                 535                 540

Asp Gln Ser Tyr Ile Asp Val Leu Pro Glu Phe Arg Asp Ser Tyr Pro
545                 550                 555                 560

Ile Lys Tyr Val His Ala Phe Glu Ser Asn Asn Phe Ile Tyr Phe Leu
            565                 570                 575

Thr Val Gln Arg Glu Thr Leu Asp Ala Gln Thr Phe His Thr Arg Ile
            580                 585                 590

Ile Arg Phe Cys Ser Ile Asn Ser Gly Leu His Ser Tyr Met Glu Met
            595                 600                 605

Pro Leu Glu Cys Ile Leu Thr Glu Lys Arg Lys Lys Arg Ser Thr Lys
610                 615                 620

Lys Glu Val Phe Asn Ile Leu Gln Ala Ala Tyr Val Ser Lys Pro Gly
625                 630                 635                 640

Ala Gln Leu Ala Arg Gln Ile Gly Ala Ser Leu Asn Asp Asp Ile Leu
            645                 650                 655

Phe Gly Val Phe Ala Gln Ser Lys Pro Asp Ser Ala Glu Pro Met Asp
            660                 665                 670

Arg Ser Ala Met Cys Ala Phe Pro Ile Lys Tyr Val Asn Asp Phe Phe
            675                 680                 685

Asn Lys Ile Val Asn Lys Asn Val Arg Cys Leu Gln His Phe Tyr
            690                 695                 700

Gly Pro Asn His Glu His Cys Phe Asn Arg Thr Leu Leu Arg Asn Ser
705                 710                 715                 720

Ser Gly Cys Glu Ala Arg Arg Asp Glu Tyr Arg Thr Glu Phe Thr Thr
            725                 730                 735

Ala Leu Gln Arg Val Asp Leu Phe Met Gly Gln Phe Ser Glu Val Leu
            740                 745                 750

Leu Thr Ser Ile Ser Thr Phe Ile Lys Gly Asp Leu Thr Ile Ala Asn
            755                 760                 765

Leu Gly Thr Ser Glu Gly Arg Phe Met Gln Val Val Val Ser Arg Ser
770                 775                 780
```

-continued

```
Gly Pro Ser Thr Pro His Val Asn Phe Leu Leu Asp Ser His Pro Val
785                 790                 795                 800

Ser Pro Glu Val Ile Val Glu His Thr Leu Asn Gln Asn Gly Tyr Thr
                805                 810                 815

Leu Val Ile Thr Gly Lys Lys Ile Thr Lys Ile Pro Leu Asn Gly Leu
                820                 825                 830

Gly Cys Arg His Phe Gln Ser Cys Ser Gln Cys Leu Ser Ala Pro Pro
                835                 840                 845

Phe Val Gln Cys Gly Trp Cys His Asp Lys Cys Val Arg Ser Glu Glu
850                 855                 860

Cys Leu Ser Gly Thr Trp Thr Gln Gln Ile Cys Leu Pro Ala Ile Tyr
865                 870                 875                 880

Lys Val Phe Pro Asn Ser Ala Pro Leu Glu Gly Gly Thr Arg Leu Thr
                885                 890                 895

Ile Cys Gly Trp Asp Phe Gly Phe Arg Arg Asn Asn Lys Phe Asp Leu
                900                 905                 910

Lys Lys Thr Arg Val Leu Leu Gly Asn Glu Ser Cys Thr Leu Thr Leu
                915                 920                 925

Ser Glu Ser Thr Met Asn Thr Leu Lys Cys Thr Val Gly Pro Ala Met
930                 935                 940

Asn Lys His Phe Asn Met Ser Ile Ile Ile Ser Asn Gly His Gly Thr
945                 950                 955                 960

Thr Gln Tyr Ser Thr Phe Ser Tyr Val Asp Pro Val Ile Thr Ser Ile
                965                 970                 975

Ser Pro Lys Tyr Gly Pro Met Ala Gly Gly Thr Leu Leu Thr Leu Thr
                980                 985                 990

Gly Asn Tyr Leu Asn Ser Gly Asn Ser Arg His Ile Ser Ile Gly Gly
                995                 1000                1005

Lys Thr Cys Thr Leu Lys Ser Val Ser Asn Ser Ile Leu Glu Cys
    1010                1015                1020

Tyr Thr Pro Ala Gln Thr Ile Ser Thr Glu Phe Ala Val Lys Leu
    1025                1030                1035

Lys Ile Asp Leu Ala Asn Arg Glu Thr Ser Ile Phe Ser Tyr Arg
    1040                1045                1050

Glu Asp Pro Ile Val Tyr Glu Ile His Pro Thr Lys Ser Phe Ile
    1055                1060                1065

Ser Gly Gly Ser Thr Ile Thr Gly Val Gly Lys Asn Leu Asn Ser
    1070                1075                1080

Val Ser Val Pro Arg Met Val Ile Asn Val His Glu Ala Gly Arg
    1085                1090                1095

Asn Phe Thr Val Ala Cys Gln His Arg Ser Asn Ser Glu Ile Ile
    1100                1105                1110

Cys Cys Thr Thr Pro Ser Leu Gln Gln Leu Asn Leu Gln Leu Pro
    1115                1120                1125

Leu Lys Thr Lys Ala Phe Phe Met Leu Asp Gly Ile Leu Ser Lys
    1130                1135                1140

Tyr Phe Asp Leu Ile Tyr Val His Asn Pro Val Phe Lys Pro Phe
    1145                1150                1155

Glu Lys Pro Val Met Ile Ser Met Gly Asn Glu Asn Val Leu Glu
    1160                1165                1170

Ile Lys Gly Asn Asp Ile Asp Pro Glu Ala Val Lys Gly Glu Val
    1175                1180                1185
```

-continued

```
Leu Lys Val Gly Asn Lys Ser Cys Glu Asn Ile His Leu His Ser
    1190            1195                1200

Glu Ala Val Leu Cys Thr Val Pro Asn Asp Leu Leu Lys Leu Asn
    1205            1210                1215

Ser Glu Leu Asn Ile Glu Trp Lys Gln Ala Ile Ser Ser Thr Val
    1220            1225                1230

Leu Gly Lys Val Ile Val Gln Pro Asp Gln Asn Phe Thr Gly Leu
    1235            1240                1245

Ile Ala Gly Val Val Ser Ile Ser Thr Ala Leu Leu Leu Leu Leu
    1250            1255                1260

Gly Phe Phe Leu Trp Leu Lys Lys Arg Lys Gln Ile Lys Asp Leu
    1265            1270                1275

Gly Ser Glu Leu Val Arg Tyr Asp Ala Arg Val His Thr Pro His
    1280            1285                1290

Leu Asp Arg Leu Val Ser Ala Arg Ser Val Ser Pro Thr Thr Glu
    1295            1300                1305

Met Val Ser Asn Glu Ser Val Asp Tyr Arg Ala Thr Phe Pro Glu
    1310            1315                1320

Asp Gln Phe Pro Asn Ser Ser Gln Asn Gly Ser Cys Arg Gln Val
    1325            1330                1335

Gln Tyr Pro Leu Thr Asp Met Ser Pro Ile Leu Thr Ser Gly Asp
    1340            1345                1350

Ser Asp Ile Ser Ser Pro Leu Leu Gln Asn Thr Val His Ile Asp
    1355            1360                1365

Leu Ser Ala Leu Asn Pro Glu Leu Val Gln Ala Val Gln His Val
    1370            1375                1380

Val Ile Gly Pro Ser Ser Leu Ile Val His Phe Asn Glu Val Ile
    1385            1390                1395

Gly Arg Gly His Phe Gly Cys Val Tyr His Gly Thr Leu Leu Asp
    1400            1405                1410

Asn Asp Gly Lys Lys Ile His Cys Ala Val Lys Ser Leu Asn Arg
    1415            1420                1425

Ile Thr Asp Ile Gly Glu Val Ser Gln Phe Leu Thr Glu Gly Ile
    1430            1435                1440

Ile Met Lys Asp Phe Ser His Pro Asn Val Leu Ser Leu Leu Gly
    1445            1450                1455

Ile Cys Leu Arg Ser Glu Gly Ser Pro Leu Val Val Leu Pro Tyr
    1460            1465                1470

Met Lys His Gly Asp Leu Arg Asn Phe Ile Arg Asn Glu Thr His
    1475            1480                1485

Asn Pro Thr Val Lys Asp Leu Ile Gly Phe Gly Leu Gln Val Ala
    1490            1495                1500

Lys Gly Met Lys Tyr Leu Ala Ser Lys Lys Phe Val His Arg Asp
    1505            1510                1515

Leu Ala Ala Arg Asn Cys Met Leu Asp Glu Lys Phe Thr Val Lys
    1520            1525                1530

Val Ala Asp Phe Gly Leu Ala Arg Asp Met Tyr Asp Lys Glu Tyr
    1535            1540                1545

Tyr Ser Val His Asn Lys Thr Gly Ala Lys Leu Pro Val Lys Trp
    1550            1555                1560

Met Ala Leu Glu Ser Leu Gln Thr Gln Lys Phe Thr Thr Lys Ser
    1565            1570                1575
```

```
Asp Val Trp Ser Phe Gly Val Leu Leu Trp Glu Leu Met Thr Arg
    1580            1585                1590

Gly Ala Pro Pro Tyr Pro Asp Val Asn Thr Phe Asp Ile Thr Val
    1595                1600                1605

Tyr Leu Leu Gln Gly Arg Arg Leu Leu Gln Pro Glu Tyr Cys Pro
    1610                1615                1620

Asp Pro Leu Tyr Glu Val Met Leu Lys Cys Trp His Pro Lys Ala
    1625                1630                1635

Glu Met Arg Pro Ser Phe Ser Glu Leu Val Ser Arg Ile Ser Ala
    1640                1645                1650

Ile Phe Ser Thr Phe Ile Gly Glu His Tyr Val His Val Asn Ala
    1655                1660                1665

Thr Tyr Val Asn Val Lys Cys Val Ala Pro Tyr Pro Ser Leu Leu
    1670                1675                1680

Ser Ser Glu Asp Asn Ala Asp Asp Glu Val Asp Thr Arg Pro Ala
    1685                1690                1695

Ser Phe Trp Glu Thr Ser
    1700

<210> SEQ ID NO 7
<211> LENGTH: 4245
<212> TYPE: DNA
<213> ORGANISM: human
<220> FEATURE:
<223> OTHER INFORMATION: Fusion protein ZM1-2 cDNA

<400> SEQUENCE: 7
atgcgaatcc taaagcgttt cctcgcttgc attcagctcc tctgtgtttg ccgcctggat      60
aaacctctca taatgaaggc ccccgctgtg cttgcacctg catcctcgt gctcctgttt     120 accttggtgc agaggagcaa tgggagtgt aaagaggcac tagcaaagtc cgagatgaat     180
gtgaatatga agtatcagct tcccaacttc accgcggaaa cacccatcca gaatgtcatt     240
ctacatgagc atcacatttt ccttggtgcc actaactaca tttatgtttt aaatgaggaa     300
gaccttcaga aggttgctga gtacaagact gggcctgtgc tggaacaccc agattgtttc     360
ccatgtcagg actgcagcag caaagccaat ttatcaggag tgtttggaa agataacatc     420 aacatggctc tagttgtcga cacctactat gatgatcaac tcattagctg tggcagcgtc     480
aacagaggga cctgccagcg acatgtcttt cccacaatc atactgctga catacagtcg     540
gaggttcact gcatattctc cccacagata gaagagccca gccagtgtcc tgactgtgtg     600
gtgagcgccc tgggagccaa agtcctttca tctgtaaagg accggttcat caacttcttt     660
gtaggcaata ccataaattc ttcttatttc ccagatcatc cattgcattc gatatcagtg     720
agaaggctaa aggaaacgaa gatgggtttt atgttttga cggaccagtc ctacattgat     780
gttttacctg agtcagaga ttcttacccc attaagtatg tccatgcctt tgaaagcaac     840
aattttattt acttcttgac ggtccaaagg gaaactctag atgctcagac ttttcacaca     900
agaataatca ggttctgttc cataaactct ggattgcatt cctacatgga aatgcctctg     960
gagtgtattc tcacagaaaa gagaaaaaag agatccacaa gaaggaagt gtttaatata    1020 cttcaggctg cgtatgtcag caagcctggg gcccagcttg ctagacaaat aggagccagc    1080
ctgaatgatg acattctttt cggggtgttc gcacaaagca agccagattc tgccgaacca    1140
atggatcgat ctgccatgtg tgcattccct atcaaatatg tcaacgactt cttcaacaag    1200
atcgtcaaca aaaacaatgt gagatgtctc cagcattttt acggacccaa tcatgagcac    1260
```

```
tgctttaata ggacacttct gagaaattca tcaggctgtg aagcgcgccg tgatgaatat      1320
cgaacagagt ttaccacagc tttgcagcgc gttgacttat tcatgggtca attcagcgaa      1380
gtcctcttaa catctatatc caccttcatt aaaggagacc tcaccatagc taatcttggg      1440
acatcagagg gtcgcttcat gcaggttgtg gtttctcgat caggaccatc aaccccctcat     1500 gtgaattttc tcctggactc ccatccagtg tctccagaag tgattgtgga gcatacatta     1560
aaccaaaatg gctacacact ggttatcact gggaagaaga tcacgaagat cccattgaat     1620
ggcttgggct gcagacattt ccagtcctgc agtcaatgcc tctctgcccc acccctttgtt    1680 cagtgtggct ggtgccacga caaatgtgtg cgatcggagg aatgcctgag cgggacatgg     1740
actcaacaga tctgtctgcc tgcaatctac aaggttttcc caaatagtgc accccttgaa     1800
ggagggacaa ggctgaccat atgtggctgg actttggat ttcggaggaa taataaattt       1860
gatttaaaga aaactagagt tctccttgga aatgagagct gcaccttgac tttaagtgag     1920
agcacgatga atacattgaa atgcacagtt ggtcctgcca tgaataagca tttcaatatg     1980
tccataatta tttcaaatgg ccacgggaca acacaataca gtacattctc ctatgtggat     2040
cctgtaataa caagtatttc gccgaaatac ggtcctatgg ctggtggcac tttacttact    2100
ttaactggaa attacctaaa cagtgggaat tctagacaca tttcaattgg tggaaaaaca     2160
tgtactttaa aaagtgtgtc aaacagtatt cttgaatgtt ataccccagc ccaaaccatt    2220
tcaactgagt ttgctgttaa attgaaaatt gacttagcca accgagagac aagcatcttc   2280
agttaccgtg aagatcccat tgtctatgaa attcatccaa ccaaatcttt tattagtggt    2340
gggagcacaa taacaggtgt tgggaaaaac ctgaattcag ttagtgtccc gagaatggtc    2400
ataaatgtgc atgaagcagg aaggaacttt acagtggcat gtcaacatcg ctctaattca   2460
gagataatct gttgtaccac tccttccctg caacagctga atctgcaact ccccctgaaa    2520
accaaagcct ttttcatgtt agatgggatc cttttccaaat actttgatct catttatgta   2580
cataatcctg tgtttaagcc ttttgaaaag ccagtgatga tctcaatggg caatgaaaat   2640
gtactggaaa ttaagggaaa tgatattgac cctgaagcag ttaaaggtga agtgttaaaa     2700
gttggaaata gagctgtga gaatatacac ttacattctg aagccgtttt atgcacggtc     2760
cccaatgacc tgctgaaatt gaacagcgag ctaaatatag agtggaagca agcaatttct    2820
tcaaccgtcc ttggaaaagt aatagttcaa ccagatcaga atttcacagg attgattgct    2880
ggtgttgtct caatatcaac agcactgtta ttactacttg ggtttttcct gtggctgaaa    2940
aagagaaagc aaattaaaga tctgggcagt gaattagttc gctacgatgc aagagtacac     3000
actcctcatt tggataggct tgtaagtgcc cgaagtgtaa gcccaactac agaaatggtt    3060
tcaaatgaat ctgtagacta ccgagctact tttccagaag atcagtttcc taattcatct   3120
cagaacggtt catgccgaca agtgcagtat cctctgacag acatgtcccc catcctaact    3180 agtgggact ctgatatatc cagtccatta ctgcaaaata ctgtccacat tgacctcagt     3240
gctctaaatc cagagctggt ccaggcagtg cagcatgtag tgattgggcc cagtagcctg    3300
attgtgcatt tcaatgaagt cataggaaga gggcattttg gttgtgtata tcatgggact    3360
ttgttggaca tgatggcaa gaaaattcac tgtgctgtga atccttgaa cagaatcact      3420 gacataggag aagtttccca atttctgacc gagggaatca tcatgaaaga ttttagtcat    3480
cccaatgtcc tctcgctcct gggaatctgc ctgcgaagtg aagggtctcc gctggtggtc   3540
ctaccataca tgaaacatgg agatcttcga aatttcattc gaaatgagac tcataatcca    3600
actgtaaaag atcttattgg ctttggtctt caagtagcca aaggcatgaa atatcttgca    3660
```

| | |
|---|---|
| agcaaaaagt tgtccacag agacttggct gcaagaaact gtatgctgga tgaaaaattc | 3720 |
| acagtcaagg ttgctgattt tggtcttgcc agagacatgt atgataaaga atactatagt | 3780 |
| gtacacaaca aaacaggtgc aaagctgcca gtgaagtgga tggctttgga agtctgcaa | 3840 |
| actcaaaagt ttaccaccaa gtcagatgtg tggtcctttg gcgtgctcct ctgggagctg | 3900 |
| atgacaagag gagccccacc ttatcctgac gtaaacacct ttgatataac tgtttacttg | 3960 |
| ttgcaaggga gaagactcct acaacccgaa tactgcccag accccttata tgaagtaatg | 4020 |
| ctaaaatgct ggcaccctaa agccgaaatg cgcccatcct tttctgaact ggtgtcccgg | 4080 |
| atatcagcga tcttctctac tttcattggg gagcactatg tccatgtgaa cgctacttat | 4140 |
| gtgaacgtaa aatgtgtcgc tccgtatcct tctctgttgt catcagaaga taacgctgat | 4200 |
| gatgaggtgg acacacgacc agcctccttc tgggagacat catag | 4245 |

<210> SEQ ID NO 8
<211> LENGTH: 4311
<212> TYPE: DNA
<213> ORGANISM: human
<220> FEATURE:
<223> OTHER INFORMATION: Fusion protein ZM2-2 cDNA

<400> SEQUENCE: 8

| | |
|---|---|
| atgcgaatcc taaagcgttt cctcgcttgc attcagctcc tctgtgtttg ccgcctggat | 60 |
| tgggctaatg gatactacag acaacagaga aaacttgttg aagagattgg ctggtcctat | 120 |
| acagataaac ctctcataat gaaggccccc gctgtgcttg cacctggcat cctcgtgctc | 180 |
| ctgtttacct tggtgcagag gagcaatggg gagtgtaaag aggcactagc aaagtccgag | 240 |
| atgaatgtga atatgaagta tcagcttccc aacttcaccg cggaaacacc catccagaat | 300 |
| gtcattctac atgagcatca cattttcctt ggtgccacta actacatttta tgttttaaat | 360 |
| gaggaagacc ttcagaaggt tgctgagtac aagactgggc tgtgctgga cacccagat | 420 |
| tgtttcccat gtcaggactg cagcagcaaa gccaatttat caggaggtgt ttggaaagat | 480 |
| aacatcaaca tggctctagt tgtcgacacc tactatgatg atcaactcat tagctgtggc | 540 |
| agcgtcaaca gagggacctg ccagcgacat gtctttcccc acaatcatac tgctgacata | 600 |
| cagtcggagg ttcactgcat attctcccca cagatagaag agcccagcca gtgtcctgac | 660 |
| tgtgtggtga gcgccctggg agccaaagtc ctttcatctg taaggaccg gttcatcaac | 720 |
| ttctttgtag gcaataccat aaattcttct tatttcccag atcatccatt gcattcgata | 780 |
| tcagtgagaa ggctaaagga aacgaaagat ggttttatgt ttttgacgga ccagtcctac | 840 |
| attgatgttt tacctgagtt cagagattct taccccatta gtatgtcca tgcctttgaa | 900 |
| agcaacaatt ttatttactt cttgacggtc aaagggaaa ctctagatgc tcagacttt | 960 |
| cacacaagaa taatcaggtt ctgttccata aactctggat tgcattccta catggaaatg | 1020 |
| cctctggagt gtattctcac agaaaagaga aaaagagat ccacaaagaa ggaagtgttt | 1080 |
| aatatacttc aggctgcgta tgtcagcaag cctggggccc agcttgctag acaaatagga | 1140 |
| gccagcctga atgatgacat tcttttcggg gtgttcgcac aaagcaagcc agattctgcc | 1200 |
| gaaccaatgg atcgatctgc catgtgtgca ttccctatca aatatgtcaa cgacttcttc | 1260 |
| aacaagatcg tcaacaaaaa caatgtgaga tgtctccagc attttacgg acccaatcat | 1320 |
| gagcactgct ttaataggac acttctgaga aattcatcag ctgtgaagc gcgccgtgat | 1380 |
| gaatatcgaa cagagtttac cacagctttg cagcgcgttg acttattcat gggtcaattc | 1440 |
| agcgaagtcc tcttaacatc tatatccacc ttcattaaag gagacctcac catagctaat | 1500 |

```
cttgggacat cagagggtcg cttcatgcag gttgtggttt ctcgatcagg accatcaacc   1560
cctcatgtga attttctcct ggactcccat ccagtgtctc cagaagtgat tgtggagcat   1620
acattaaacc aaaatggcta cacactggtt atcactggga agaagatcac gaagatccca   1680
ttgaatggct tgggctgcag acatttccag tcctgcagtc aatgcctctc tgccccaccc   1740
tttgttcagt gtggctggtg ccacgacaaa tgtgtgcgat cggaggaatg cctgagcggg   1800
acatggactc aacagatctg tctgcctgca atctacaagg ttttcccaaa tagtgcaccc   1860
cttgaaggag ggacaaggct gaccatatgt ggctgggact ttggatttcg gaggaataat   1920
aaatttgatt taaagaaaac tagagttctc cttggaaatg agagctgcac cttgactttc   1980
agtgagagca cgatgaatac attgaaatgc acagttggtc ctgccatgaa taagcatttc   2040
aatatgtcca taattatttc aaatggccac gggacaacac aatacagtac attctcctat   2100
gtggatcctg taataacaag tatttcgccg aaatacggtc ctatggctgg tggcacttta   2160
cttactttaa ctggaaatta cctaaacagt gggaattcta gacacatttc aattggtgga   2220
aaaacatgta ctttaaaaag tgtgtcaaac agtattcttg aatgttatac cccagcccaa   2280
accatttcaa ctgagtttgc tgttaaattg aaaattgact tagccaaccg agagacaagc   2340
atcttcagtt accgtgaaga tcccattgtc tatgaaattc atccaaccaa atcttttatt   2400
agtggtggga gcacaataac aggtgttggg aaaaacctga attcagttag tgtcccgaga   2460
atggtcataa atgtgcatga agcaggaagg aactttacag tggcatgtca acatcgctct   2520
aattcagaga taatctgttg taccactcct tccctgcaac agctgaatct gcaactcccc   2580
ctgaaaacca aagcctttt catgttagat gggatccttt ccaaatactt tgatctcatt   2640
tatgtacata atcctgtgtt taagccttt gaaaagccag tgatgatctc aatgggcaat   2700
gaaaatgtac tggaaattaa gggaaatgat attgaccctg aagcagttaa aggtgaagtg   2760
ttaaaagttg gaaataagag ctgtgagaat atacacttac attctgaagc cgtttttatgc  2820 acggtcccca atgacctgct gaaattgaac agcgagctaa atatagagtg gaagcaagca   2880
atttcttcaa ccgtccttgg aaaagtaata gttcaaccag atcagaattt cacaggattg   2940
attgctggtg ttgtctcaat atcaacagca ctgttattac tacttgggtt tttcctgtgg   3000
ctgaaaaaga gaaagcaaat taaagatctg ggcagtgaat tagttcgcta cgatgcaaga   3060
gtacacactc ctcatttgga taggcttgta agtgcccgaa gtgtaagccc aactacagaa   3120
atggtttcaa atgaatctgt agactaccga gctacttttc cagaagatca gtttcctaat   3180
tcatctcaga acggttcatg ccgacaagtg cagtatcctc tgacagacat gtcccccatc   3240
ctaactagtg gggactctga tatatccagt ccattactgc aaaatactgt ccacattgac   3300
ctcagtgctc taaatccaga gctggtccag gcagtcagc atgtagtgat tgggcccagt   3360
agcctgattg tgcatttcaa tgaagtcata ggaagagggc attttggttg tgtatatcat   3420
gggactttgt tggacaatga tggcaagaaa attcactgtg ctgtgaaatc cttgaacaga   3480
atcactgaca taggagaagt ttcccaattt ctgaccgagg gaatcatcat gaaagatttt   3540
agtcatccca atgtcctctc gctcctggga atctgcctgc aagtgaagg gtctccgctg   3600 gtggtcctac catacatgaa acatggagat cttcgaaatt tcattcgaaa tgagactcat   3660
aatccaactg taaagatct tattggcttt ggtcttcaag tagccaaagg catgaaatat   3720
cttgcaagca aaaagtttgt ccacagagac ttggctgcaa gaaactgtat gctggatgaa   3780
aaattcacag tcaaggttgc tgattttggt cttgccagag acatgtatga taagaatac   3840 tatagtgtac acaacaaaac aggtgcaaag ctgccagtga agtggatggc tttggaaagt   3900
```

```
ctgcaaactc aaaagtttac caccaagtca gatgtgtggt cctttggcgt gctcctctgg    3960
gagctgatga caagaggagc cccacccttat cctgacgtaa acacctttga tataactgtt   4020
tacttgttgc aagggagaag actcctacaa cccgaatact gcccagaccc cttatatgaa    4080
gtaatgctaa aatgctggca ccctaaagcc gaaatgcgcc catccttttc tgaactggtg    4140
tcccggatat cagcgatctt ctctactttc attggggagc actatgtcca tgtgaacgct    4200
acttatgtga acgtaaaatg tgtcgctccg tatccttctc tgttgtcatc agaagataac    4260
gctgatgatg aggtggacac acgaccagcc tccttctggg agacatcata g             4311

<210> SEQ ID NO 9
<211> LENGTH: 4491
<212> TYPE: DNA
<213> ORGANISM: human
<220> FEATURE:
<223> OTHER INFORMATION: Fusion protein ZM3-2 cDNA

<400> SEQUENCE: 9
atgcgaatcc taaagcgttt cctcgcttgc attcagctcc tctgtgtttg ccgcctggat      60
tgggctaatg gatactacag acaacagaga aaacttgttg aagagattgg ctggtcctat    120
acaggagcac tgaatcaaaa aaattgggga agaaatatc caacatgtaa tagcccaaaa     180
caatctccta tcaatattga tgaagatctt acacaagtaa atgtgaatct taagaaactt    240
aaatttcagg gttgggataa acatcattg gaaaacacat tcattcataa cactgggaaa     300
acagataaac ctctcataat gaaggccccc gctgtgcttg cacctggcat cctcgtgctc    360
ctgtttacct tggtgcagag gagcaatggg gagtgtaaag aggcactagc aaagtccgag    420
atgaatgtga atatgaagta tcagcttccc aacttcaccg cggaaacacc catccagaat    480
gtcattctac atgagcatca cattttcctt ggtgccacta actacattta tgtttttaat    540
gaggaagacc ttcagaaggt tgctgagtac aagactgggc ctgtgctgga cacccagat    600 tgtttcccat gtcaggactg cagcagcaaa gccaatttat caggaggtgt ttggaaagat    660
aacatcaaca tggctctagt tgtcgacacc tactatgatg atcaactcat tagctgtggc    720
agcgtcaaca gagggacctg ccagcgacat gtctttcccc acaatcatac tgctgacata    780
cagtcggagg ttcactgcat attctcccca cagatagaag agcccagcca gtgtcctgac    840
tgtgtggtga cgccctggg agccaaagtc ctttcatctg taaggaccg gttcatcaac    900 ttctttgtag gcaataccat aaattcttct tatttcccag atcatccatt gcattcgata    960
tcagtgagaa ggctaaagga acgaaagat ggttttatgt ttttgacgga ccagtcctac   1020
attgatgttt tacctgagtt cagagattct taccccatta gtatgtcca tgcctttgaa    1080 agcaacaatt ttatttactt cttgacggtc caaagggaaa ctctagatgc tcagactttt    1140
cacacaagaa taatcaggtt ctgttccata aactctggat tgcattccta catggaaatg   1200
cctctggagt gtattctcac agaaaagaga aaaagagat ccacaaagaa ggaagtgttt    1260
aatatacttc aggctgcgta tgtcagcaag cctgggccc agcttgctag acaaatagga    1320
gccagcctga atgatgacat tcttttcggg gtgttcgcac aaagcaagcc agattctgcc    1380
gaaccaatgg atcgatctgc catgtgtgca ttccctatca aatatgtcaa cgacttcttc    1440
aacaagatcg tcaacaaaaa caatgtgaga tgtctccagc atttttacgg acccaatcat    1500
gagcactgct ttaataggac acttctgaga aattcatcag ctgtgaagc gcgccgtgat    1560 gaatatcgaa cagagtttac cacagctttg cagcgcgttg acttattcat gggtcaattc    1620
agcgaagtcc tcttaacatc tatatccacc ttcattaaag gagacctcac catagctaat    1680
```

```
cttgggacat cagagggtcg cttcatgcag gttgtggttt ctcgatcagg accatcaacc    1740
cctcatgtga attttctcct ggactcccat ccagtgtctc cagaagtgat tgtggagcat    1800
acattaaacc aaaatggcta cacactggtt atcactggga agaagatcac gaagatccca    1860
ttgaatggct tgggctgcag acatttccag tcctgcagtc aatgcctctc tgccccaccc    1920
tttgttcagt gtggctggtg ccacgacaaa tgtgtgcgat cggaggaatg cctgagcggg    1980
acatggactc aacagatctg tctgcctgca atctacaagg ttttcccaaa tagtgcaccc    2040
cttgaaggag ggacaaggct gaccatatgt ggctgggact ttggatttcg gaggaataat    2100
aaatttgatt taaagaaaac tagagttctc cttggaaatg agagctgcac cttgacttta    2160
agtgagagca cgatgaatac attgaaatgc acagttggtc ctgccatgaa taagcatttc    2220
aatatgtcca taattatttc aaatggccac gggacaacac aatacagtac attctcctat    2280
gtggatcctg taataacaag tatttcgccg aaatacggtc ctatggctgg tggcacttta    2340
cttactttaa ctggaaatta cctaaacagt gggaattcta gacacatttc aattggtgga    2400
aaaacatgta ctttaaaaag tgtgtcaaac agtattcttg aatgttatac cccagcccaa    2460
accatttcaa ctgagtttgc tgttaaattg aaaattgact tagccaaccg agagacaagc    2520
atcttcagtt accgtgaaga tcccattgtc tatgaaattc atccaaccaa atctttatt    2580 agtggtggga gcacaataac aggtgttggg aaaaacctga attcagttag tgtcccgaga    2640
atggtcataa atgtgcatga agcaggaagg aactttacag tggcatgtca acatcgctct    2700
aattcagaga taatctgttg taccactcct tccctgcaac agctgaatct gcaactcccc    2760
ctgaaaacca agccttttt catgttagat gggatccttt ccaaatactt tgatctcatt    2820
tatgtacata atcctgtgtt taagccttt gaaaagccag tgatgatctc aatgggcaat    2880
gaaaatgtac tggaaattaa gggaaatgat attgaccctg aagcagttaa aggtgaagtg    2940
ttaaaagttg gaaataagag ctgtgagaat atacacttac attctgaagc cgttttatgc    3000
acggtcccca tgaccctgct gaaattgaac agcgagctaa atatagagtg gaagcaagca    3060
atttcttcaa ccgtccttgg aaaagtaata gttcaaccag atcagaattt cacaggattg    3120
attgctggtg ttgtctcaat atcaacagca ctgttattac tacttgggtt tttcctgtgg    3180
ctgaaaaaga gaaagcaaat taaagatctg ggcagtgaat tagttcgcta cgatgcaaga    3240
gtacacactc ctcatttgga taggcttgta agtgcccgaa gtgtaagccc aactacagaa    3300
atggtttcaa atgaatctgt agactaccga gctactttc cagaagatca gtttcctaat    3360
tcatctcaga acggttcatg ccgacaagtg cagtatcctc tgacagacat gtcccccatc    3420
ctaactagtg gggactctga tatatccagt ccattactgc aaaatactgt ccacattgac    3480
ctcagtgctc taaatccaga gctggtccag gcagtcagc atgtagtgat tgggcccagt    3540
agcctgattg tgcatttcaa tgaagtcata ggaagagggc attttggttg tgtatatcat    3600
gggactttgt tggacaatga tggcaagaaa attcactgtg ctgtgaaatc cttgaacaga    3660
atcactgaca taggagaagt ttcccaattt ctgaccgagg gaatcatcat gaaagatttt    3720
agtcatccca atgtcctctc gctcctggga atctgcctgc gaagtgaagg gtctccgctg    3780
gtggtcctac catacatgaa acatggagat cttcgaaatt tcattcgaaa tgagactcat    3840
aatccaactg taaaagatct tattggcttt ggtcttcaag tagccaaagg catgaaatat    3900
cttgcaagca aaaagtttgt ccacagagac ttggctgcaa gaaactgtat gctggatgaa    3960
aaattcacag tcaaggttgc tgattttggt cttgccagag acatgtatga taaagaatac    4020
tatagtgtac acaacaaaac aggtgcaaag ctgccagtga agtggatggc tttggaaagt    4080
```

-continued

```
ctgcaaactc aaaagtttac caccaagtca gatgtgtggt cctttggcgt gctcctctgg      4140
gagctgatga caagaggagc cccaccttat cctgacgtaa acacctttga tataactgtt      4200
tacttgttgc aagggagaag actcctacaa cccgaatact gcccagaccc cttatatgaa      4260
gtaatgctaa aatgctggca ccctaaagcc gaaatgcgcc catccttttc tgaactggtg      4320
tcccggatat cagcgatctt ctctactttc attggggagc actatgtcca tgtgaacgct      4380
acttatgtga acgtaaaatg tgtcgctccg tatccttctc tgttgtcatc agaagataac      4440
gctgatgatg aggtggacac acgaccagcc tccttctggg agacatcata g                4491
```

<210> SEQ ID NO 10
<211> LENGTH: 5115
<212> TYPE: DNA
<213> ORGANISM: human
<220> FEATURE:
<223> OTHER INFORMATION: Fusion protein ZM8-2 cDNA

<400> SEQUENCE: 10

```
atgcgaatcc taaagcgttt cctcgcttgc attcagctcc tctgtgtttg ccgcctggat        60
tgggctaatg gatactacag acaacagaga aaacttgttg aagagattgg ctggtcctat       120
acaggagcac tgaatcaaaa aaattgggga agaaatatc caacatgtaa tagcccaaaa       180
caatctccta tcaatattga tgaagatctt acacaagtaa atgtgaatct taagaaactt       240
aaatttcagg gttgggataa acatcattg gaaaacacat tcattcataa cactgggaaa       300
acagtggaaa ttaatctcac taatgactac cgtgtcagcg aggagtttca gaaatggtg       360 tttaaagcaa gcaagataac ttttcactgg ggaaaatgca atatgtcatc tgatggatca       420
gagcatagtt tagaaggaca aaaatttcca cttgagatgc aaatctactg ctttgatgcg       480
gaccgatttt caagttttga ggaagcagtc aaaggaaaag ggaagttaag agctttatcc       540
attttgtttg aggttgggac agaagaaaat ttggatttca aagcgattat tgatggagtc       600
gaaagtgtta gtcgttttgg gaagcaggct gctttagatc cattcatact gttgaacctt       660 ctgccaaaact caactgacaa gtattacatt tacaatggct cattgacatc tcctccctgc       720
acagacacag ttgactggat tgtttttaaa gatacagtta gcatctctga agccagttg        780 gctgtttttt gtgaagttct tacaatgcaa caatctggtt atgtcatgct gatggactac       840
ttacaaaaca attttcgaga gcaacagtac aagttctcta gacaggtgtt ttcctcatac       900
actggaaagg aagagattca tgaagcagat aaacctctca taatgaaggc cccgctgtg       960 cttgcacctg gcatcctcgt gctcctgttt accttggtgc agaggagcaa tgggggagtgt     1020 aaagaggcac tagcaaagtc cgagatgaat gtgaatatga agtatcagct tcccaacttc      1080
accgcggaaa cacccatcca gaatgtcatt ctacatgagc atcacatttt ccttggtgcc      1140
actaactaca tttatgtttt aaatgaggaa gaccttcaga aggttgctga gtacaagact      1200
gggcctgtgc tggaacaccc agattgtttc ccatgtcagg actgcagcag caaagccaat      1260
ttatcaggag tgtttggaa agataacatc aacatggctc tagttgtcga cacctactat      1320
gatgatcaac tcattagctg tggcagcgtc aacagaggga cctgccagcg acatgtcttt      1380
ccccacaatc atactgctga catacagtcg gaggttcact gcatattctc cccacagata      1440
gaagagccca gccagtgtcc tgactgtgtg gtgagcgccc tgggagccaa agtcctttca      1500
tctgtaaagg accggttcat caacttcttt gtaggcaata ccataaaattc ttcttatttc      1560 ccagatcatc cattgcattc gatatcagtg agaaggctaa aggaaacgaa agatggtttt      1620 atgttttga cggaccagtc ctacattgat gttttacctg agttcagaga ttcttacccc      1680
```

```
attaagtatg tccatgcctt tgaaagcaac aattttattt acttcttgac ggtccaaagg      1740
gaaactctag atgctcagac ttttcacaca agaataatca ggttctgttc cataaactct      1800
ggattgcatt cctacatgga aatgcctctg gagtgtattc tcacagaaaa gagaaaaaag      1860
agatccacaa agaaggaagt gtttaatata cttcaggctg cgtatgtcag caagcctggg      1920
gcccagcttg ctagacaaat aggagccagc ctgaatgatg acattctttt cggggtgttc      1980
gcacaaagca agccagattc tgccgaacca atggatcgat ctgccatgtg tgcattccct      2040
atcaaatatg tcaacgactt cttcaacaag atcgtcaaca aaaacaatgt gagatgtctc      2100
cagcattttt acggacccaa tcatgagcac tgctttaata ggacacttct gagaaattca      2160
tcaggctgtg aagcgcgccg tgatgaatat cgaacagagt ttaccacagc tttgcagcgc      2220
gttgacttat tcatgggtca attcagcgaa gtcctcttaa catctatatc caccttcatt      2280
aaaggagacc tcaccatagc taatcttggg acatcagagg gtcgcttcat gcaggttgtg      2340
gtttctcgat caggaccatc aacccctcat gtgaattttc tcctggactc ccatccagtg      2400
tctccagaag tgattgtgga gcatacatta aaccaaaatg ctacacact ggttatcact       2460 gggaagaaga tcacgaagat cccattgaat ggcttgggct gcagacattt ccagtcctgc      2520
agtcaatgcc tctctgcccc accctttgtt cagtgtggct ggtgccacga caaatgtgtg      2580
cgatcggagg aatgcctgag cgggacatgg actcaacaga tctgtctgcc tgcaatctac      2640
aaggttttcc caaatagtgc accccttgaa ggagggacaa ggctgaccat atgtggctgg      2700
gactttggat tcggaggaa taataaattt gatttaaaga aaactagagt tctccttgga       2760
aatgagagct gcaccttgac tttaagtgag agcacgatga atacattgaa atgcacagtt      2820
ggtcctgcca tgaataagca tttcaatatg tccataatta tttcaaatgg ccacgggaca      2880
acacaataca gtacattctc ctatgtggat cctgtaataa caagtatttc gccgaaatac      2940
ggtcctatgg ctggtggcac tttacttact ttaactggaa attacctaaa cagtgggaat      3000
tctagacaca tttcaattgg tggaaaaaca tgtactttaa aagtgtgtc aaacagtatt        3060 cttgaatgtt ataccccagc ccaaaccatt tcaactgagt ttgctgttaa attgaaaatt      3120
gacttagcca accgagagac aagcatcttc agttaccgtg aagatcccat tgtctatgaa      3180
attcatccaa ccaaatcttt tattagtggt gggagcacaa taacaggtgt tgggaaaaac      3240
ctgaattcag ttagtgtccc gagaatggtc ataaatgtgc atgaagcagg aaggaacttt      3300
acagtggcat gtcaacatcg ctctaattca gagataatct gttgtaccac tccttccctg      3360
caacagctga atctgcaact cccccctgaaa accaaagcct ttttcatgtt agatgggatc      3420 cttttccaaat actttgatct catttatgta cataatcctg tgtttaagcc ttttgaaaag      3480
ccagtgatga tctcaatggg caatgaaaat gtactggaaa ttaagggaaa tgatattgac      3540
cctgaagcag ttaaaggtga agtgttaaaa gttggaaata gagctgtga gaatatacac        3600 ttacattctg aagccgtttt atgcacggtc cccaatgacc tgctgaaatt gaacagcgag      3660
ctaaatatag agtggaagca agcaatttct tcaaccgtcc ttggaaaagt aatagttcaa      3720
ccagatcaga atttcacagg attgattgct ggtgttgtct caatatcaac agcactgtta      3780
ttactacttg gttttttcct gtggctgaaa aagagaaagc aaattaaaga tctgggcagt      3840
gaattagttc gctacgatgc aagagtacac actcctcatt tggataggct tgtaagtgcc      3900
cgaagtgtaa gcccaactac agaaatggtt tcaaatgaat ctgtagacta ccgagctact      3960
tttccagaag atcagtttcc taattcatct cagaacggtt catgccgaca agtgcagtat      4020
cctctgacag acatgtcccc catcctaact agtgggggact ctgatatatc cagtccatta      4080
```

```
ctgcaaaata ctgtccacat tgacctcagt gctctaaatc cagagctggt ccaggcagtg    4140
cagcatgtag tgattgggcc cagtagcctg attgtgcatt tcaatgaagt cataggaaga    4200
gggcattttg gttgtgtata tcatgggact ttgttggaca atgatggcaa gaaaattcac    4260
tgtgctgtga aatccttgaa cagaatcact gacataggag aagtttccca atttctgacc    4320
gagggaatca tcatgaaaga ttttagtcat cccaatgtcc tctcgctcct gggaatctgc    4380
ctgcgaagtg aagggtctcc gctggtggtc ctaccataca tgaaacatgg agatcttcga    4440
aatttcattc gaaatgagac tcataatcca actgtaaaag atcttattgg ctttggtctt    4500
caagtagcca aaggcatgaa atatcttgca agcaaaagt ttgtccacag agacttggct     4560
gcaagaaact gtatgctgga tgaaaaattc acagtcaagg ttgctgattt tggtcttgcc    4620
agagacatgt atgataaaga atactatagt gtacacaaca aaacaggtgc aaagctgcca    4680
gtgaagtgga tggctttgga aagtctgcaa actcaaaagt ttaccaccaa gtcagatgtg    4740
tggtcctttg gcgtgctcct ctgggagctg atgacaagag gagccccacc ttatcctgac    4800
gtaaacacct ttgatataac tgtttacttg ttgcaaggga gaagactcct acaacccgaa    4860
tactgcccag accccttata tgaagtaatg ctaaaatgct ggcaccctaa agccgaaatg    4920
cgcccatcct tttctgaact ggtgtcccgg atatcagcga tcttctctac tttcattggg    4980
gagcactatg tccatgtgaa cgctacttat gtgaacgtaa aatgtgtcgc tccgtatcct    5040
tctctgttgt catcagaaga taacgctgat gatgaggtgg acacacgacc agcctccttc    5100
tgggagacat catag                                                     5115

<210> SEQ ID NO 11
<211> LENGTH: 25
<212> TYPE: DNA
<213> ORGANISM: Artificial sequence
<220> FEATURE:
<223> OTHER INFORMATION: Forward primer

<400> SEQUENCE: 11
atgcgaatcc taaagcgttt cctcg                                             25

<210> SEQ ID NO 12
<211> LENGTH: 25
<212> TYPE: DNA
<213> ORGANISM: Artificial sequence
<220> FEATURE:
<223> OTHER INFORMATION: Reverse primer

<400> SEQUENCE: 12
ctatgatgtc tcccagaagg aggct                                             25
```

USES OF COMPOUND IN PREPARATION OF DRUGS FOR TREATING BRAIN GLIOMA

CROSS-REFERENCE TO RELATED APPLICATION(S)

This application is a National Phase Patent Application and claims priority to and the benefit of International Application Number PCT/CN2016/111227, filed on Dec. 21, 2016, which claims priority to Chinese Patent Application Number 201511022391.8, filed on Dec. 31, 2015, the entire contents of all of which are incorporated herein by reference.

INCORPORATION BY REFERENCE

The instant application contains a Sequence Listing which has been submitted electronically in ASCII format and is hereby incorporated by reference in its entirety. Said ASCII copy, modified May 24, 2021, is named Amended-SQL.txt and is 89,430 bytes in size.

TECHNICAL FIELD

The present invention relates to the technical field of biological medicines. Specifically, the present invention relates to use of a compound in preparation of a medicine for treating brain gliomas, in particular glioblastomas.

BACKGROUND OF THE INVENTION

Glioblastomas are the most malignant gliomas among brain gliomas. Glioblastomas grow beneath the cerebral cortex, almost found all over supratentorial cerebral hemisphere. Through infiltrative growth, glioblastomas usually invade several lobes, invade deep structures, and via corpus callosum, spread to the cerebral hemisphere on the opposite side. Glioblastomas are mostly found at the frontal lobe, followed by the temporal lobe and the parietal lobe, and in few cases seen at the occipital lobe/thalamus, basal ganglia, etc.

Glioblastomas grow fast and have short courses. 70-80% of patients experience a disease course of 3-6 months, and only 10% experience a disease course over 1 year. In rare cases, glioblastoma bleeding causes stroke-like episodes. Glioblastomas grow rapidly, resulting in evident symptoms of extensive brain edema and obvious intracranial hypertension. Almost all patients suffer from headaches, emesis, papilloedema accompanied with headache, change in mental status, limb weakness, disorder of consciousness and speech disorder. The glioblastomas lead to infiltrative damages in brain tissues, causing a series of focal symptoms, and glioblastoma patients suffer from hemiplegia, hemidysesthesia, aphasias, hemianopsia, etc., to different degrees. Hemiplegia, cranial nerve lesions, hemidysesthesia and hemianopsia can be found through neurological examination. About 33% of patients have suffered from epileptic attack, and about 20% have psychiatric symptoms such as apathy, dementia and hyphophrenia and the like.

Glioblastomas can be classified into two types, namely secondary glioblastomas which progress from lower-grade gliomas and primary glioblastomas which do not present low-grade precancerous lesions.

The primary glioblastomas are IV-grade glioblastomas when diagnosed at the first time, and their most obvious molecular characteristics include EGFR amplification, mutation or over-expression (40%), P53 mutation (30%), CDKN2A/B deletion (30-40%), RB1 mutation or deletion, loss of chromosome 10 (70%), PTEN mutation (30%), etc.

In contrast, the secondary glioblastomas are IV-grade gliomas which progress from lower-grade brain gliomas (II grade or III grade). Gliomas, which are found low-grade at the first clinical diagnosis, grow back after surgery or chemoradiotherapy and develop into IV-grade gliomas. Research has found that molecular markers and genetic cell pathways of the secondary glioblastomas are different from those of the primary glioblastomas. Mutation of isocitrate dehydrogenase (IDH) was found only in the secondary glioblastomas, but not all secondary glioblastomas have the IDH mutation. At present, the research on the molecular markers of the secondary glioblastomas focuses on the mutation of IDH 1 (70%), mutation of P53 (65%), over-expression of PDGFA and PDGFRA (60%), deletion of the long arm of chromosome 19 (50%), and mutation or deletion of RB1 (25%). The discovery of those molecular markers provides important targets for targeted treatment of the glioblastomas. There are many targeted medicines targeting at those molecular markers, but the targeted medicines do not enter clinical application for various causes. The root cause is generally that a low specificity of target relationship results in poor treatment effects and large side effects of the medicines. Therefore, those targeted medicines are not suitable for clinical application.

Therefore, for brain gliomas, in particular glioblastomas, medicines which have higher target specificity and can realize precision treatment are needed at present.

Hepatocyte growth factor receptor (HGFR, also called c-Met), is encoded by the met gene and belongs to the receptor tyrosine kinase family. After HGFR binds with its ligand hepatocyte growth factor, the intracellular domain of HGFR is automatically phosphorylated to activate downstream signaling pathway, thereby adjusting cell proliferation, morphogenesis and motility. Many c-Met abnormalities have been found, usually appearing in different tumors. In addition, research has found that phosphatase encoded by PTPRZ1 gene (belonging to receptor protein tyrosine kinase family, also called RPRPB) can remove a specific phosphorylation site from c-Met to deactivate the met signaling pathway. Thus it can be concluded that the protein may have a certain binding relationship with c-Met, and affect the role of c-Met in the occurrence and development of diseases.

SUMMARY OF THE INVENTION

Aiming at the above problems, the objective of the present invention is to provide a medicament which has high target specificity and can achieve personalized and precise treatment of brain gliomas, in particular glioblastomas.

Based on a huge amount of researches, the inventors of the present invention found that compared with other c-Met inhibitors, the compound represented by formula A, as a c-Met inhibitor, has a more obvious effect of inhibiting brain gliomas, in particular glioblastomas. In particular, the compound has a more obvious effect of inhibiting a sub-type of glioblastoma which expresses a specific fusion protein and therefore results in poorer prognosis. Accordingly, the present invention provides the following technical solutions:

The present invention provides use of the compound represented by formula A in the manufacture of a medicament for the treatment of a brain glioma.

Formula A

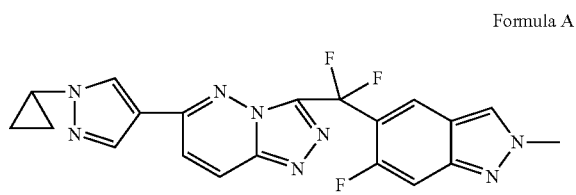 [SMILES: Cn1cc2cc(C(F)(F)c3nnc4ccc(-c5cnn(C6CC6)c5)nn34)c(F)cc2n1]

The compound represented by formula A can be synthesized by the steps and scheme as described in Example 44 of Chinese patent application publication CN103122000A.

Preferably, the brain glioma is a glioblastoma.

More preferably, the brain glioma is a secondary glioblastoma.

Research has found that, on one hand, a specific fusion protein can be expressed in a secondary glioblastoma. The fusion protein comprises a large part of the amino acid sequence of c-Met, and a part of the amino acid sequence of PTPRZ1 fused at the N-terminal of the amino acid sequence of c-Met. The compound represented by formula A has a better effect of inhibiting the proliferation and tumor formation of the sub-type of glioblastoma which expresses the fusion protein.

Therefore, preferably, the present invention provides use of the compound represented by formula A in the manufacture of a medicament for the treatment of a secondary glioblastoma, wherein the secondary glioblastoma is a subtype of secondary glioblastoma which expresses a fusion protein, and the fusion protein (also called "ZM" herein) is formed by fusing a protein portion translated from exon 1, exons 1 to 2, exons 1 to 3 or exons 1 to 8 of PTPRZ1 to a protein portion translated from exons 2 to 24 of c-Met, in which the protein portion of PTPRZ1 is located at the N-terminal of the protein portion of c-Met.

Preferably, the fusion protein comprises the amino acid sequence as shown by SEQ ID NO: 1.

Preferably, the fusion protein comprises the amino acid sequence as shown by SEQ ID NO: 2.

More preferably, the fusion protein comprises the amino acid sequence as shown by SEQ ID NO: 1 and an amino acid sequence as shown by SEQ ID NO: 2 at the N-terminal thereof.

Most preferably, the fusion protein comprises the amino acid sequence as shown by SEQ ID NO: 3, SEQ ID NO: 4, SEQ ID NO: 5, or SEQ ID NO: 6.

According to particular embodiments of the present invention, the amino acid sequence of the fusion protein is as shown by SEQ ID NO: 3, SEQ ID NO: 4, SEQ ID NO: 5, or SEQ ID NO: 6. Herein, the fusion protein whose amino acid sequence is as shown by SEQ ID NO: 3 is named as "ZM1-2"; the fusion protein whose amino acid sequence is as shown by SEQ ID NO: 4 is named as "ZM2-2"; the fusion protein whose amino acid sequence is as shown by SEQ ID NO: 5 is named as "ZM3-2"; and the fusion protein whose amino acid sequence is as shown by SEQ ID NO: 6 is named as "ZM8-2".

Based on the above technical solutions, the expression of the above mentioned fusion proteins in the present invention in glioblastoma cells can be detected with an antibody through immunoblotting. When the amino acid sequence of a protein to be detected is known, an antibody (for example, a monoclonal antibody or a multi-clonal antibody) against the protein is used to detect the expression of the protein in a specific tissue or cells by immunoblotting, which is a conventional technique in the art. The detection can be performed for a fragment of the fusion protein or the whole fusion protein. According to particular embodiments of the present invention, an antibody against human c-Met protein can be used to detect the expression of the above-mentioned fusion proteins. In fact, based on whether or not any of the fusion proteins is expressed in glioblastoma cells, glioblastomas can be subtyped and then treated with the compound represented by formula A provided by the present invention.

On the other hand, a secondary glioblastoma may contain a specific fusion transcript, and the fusion transcript contains a large part of c-Met-encoding RNAs and a part of PTPRZ1-encoding RNAs fused at the 5'-terminal of the part of c-Met-encoding RNAs. The compound represented by formula A has a better effect of inhibiting the proliferation and tumor formation of a sub-type of glioblastoma which contains the fusion transcript.

Therefore, preferably, the present invention provides use of the compound represented by formula A in the manufacture of a medicament for the treatment of a secondary glioblastoma, wherein the secondary glioblastoma is a subtype of secondary glioblastoma which contains a fusion transcript, and the fusion transcript is formed by connecting a RNA portion which is transcribed from exon 1, exons 1 to 2, exons 1 to 3 or exons 1 to 8 of PTPRZ1 and a RNA portion which is transcribed from exons 2 to 24 of c-Met, in which the RNA portion of PTPRZ1 is located at the 5'-terminal of the RNA portion of c-Met.

Preferably, the fusion transcript comprises a RNA sequence encoding the amino acid sequence as shown by SEQ ID NO: 1.

Preferably, the fusion transcript further comprises a RNA sequence encoding the amino acid sequence as shown by SEQ ID NO: 2.

More preferably, the fusion transcript comprises a RNA sequence encoding the amino acid sequence as shown by SEQ ID NO: 1, and a RNA sequence encoding the amino acid sequence as shown by SEQ ID NO: 2 at the 5'-terminal thereof.

Most preferably, the fusion transcript comprises a RNA sequence encoding the amino acid sequence as shown by SEQ ID NO: 3, SEQ ID NO: 4, SEQ ID NO: 5, or SEQ ID NO: 6. According to particular embodiments of the present invention, the nucleotide sequence of the fusion transcript is comprised of a RNA sequence encoding the amino acid sequence as shown by SEQ ID NO: 3, SEQ ID NO: 4, SEQ ID NO: 5, or SEQ ID NO: 6.

Similarly based on the above technical solutions, the expression of the above-mentioned fusion proteins in the present invention in glioblastoma cells can also be detected on the above-mentioned fusion transcripts, namely the encoding RNA sequences thereof. When the amino acid sequence of a protein to be detected is known, detecting the encoding RNA sequence also belongs to a conventional technique in the art, and the detection may be performed for a fragment of the fusion protein or the whole fusion protein. For example, total RNA can be extracted and used as a template, or total RNA can be reversely transcribed into cDNA which is used as a template. Specific primers are used to perform PCR amplification. In fact, based on whether or not the fusion transcript is present in glioblastoma cells, glioblastomas can be subtyped and then treated with the compound represented by formula A provided by the present invention.

Therefore, the present invention also provides the cDNA sequence of the fusion protein ZM1-2, ZM2-2, ZM3-2 or ZM8-2, respectively as shown by SEQ ID NO: 7, SEQ ID NO: 8, SEQ ID NO: 9 or SEQ ID NO: 10.

Based on the technical solutions provided by the present invention, the compound represented by formula A can be clinically employed to treat brain gliomas, in particular glioblastomas, including a subject in need can be administered with an effective amount of the compound represented by formula A or any pharmaceutical composition containing the compound represented by formula A. The dose and administration route depend on the individual health status, symptoms and severity of the disease and the like, and need to be judged by a doctor upon specific situations.

Specifically, when a precision treatment scheme is needed, a tumor sample, such as a glioblastoma sample of a subject to the treated can be clinically detected first, for example, to detect whether or not the above-mentioned fusion protein is expressed or the above mentioned fusion transcript is contained in the glioblastoma sample, and/or to detect the content of the fusion protein or fusion transcript in the sample. If the sample of the subject to be treated contains the above-mentioned fusion protein or fusion transcript, or if the content of the fusion protein or the fusion transcript is higher than that in a normal subject or in any other relevant sample, the compound represented by formula A or a pharmaceutical composition containing the compound can be administered. In such circumstances, the presence or content of the fusion protein or the fusion transcript in the sample can be detected using a conventional technique in the art, for example, the above-mentioned immunoblotting and PCR.

Clinical research shows that glioblastomas which express the fusion protein as mentioned in the present invention or contain the fusion transcript as mentioned in the present invention have poorer prognosis, and the survival time of those patients is obviously shorter than that of patients without the fusion protein or fusion transcrip (127 days VS 248 days). For patients with such glioblastomas, the compound represented by formula A provided by the invention has a special treatment advantage in comparison with other similar medicaments.

Moreover, during the treatment on brain gliomas, in particular glioblastomas, the compound represented by formula A can be used together with other therapies or therapeutic agents, simultaneously, sequentially or in a certain time interval. The dose and administration route depend on the individual health status, symptoms and severity of the disease and the like, and need to be judged by a doctor upon specific situations.

Compared with the prior art, the present invention has the following beneficial effects:

Through experiments of the compound represented by formula A on in-vitro proliferation and in-vivo tumorigenesis of glioblastoma cell lines, the present invention proves for the first time that the compound represented by the formula A, compared with other c-Met inhibitors, can more significantly inhibit the development of glioblastomas. Specifically speaking, experiments prove that, in comparison with c-Met inhibitors with similar structures, the compound represented by formula A has a more potent inhibitory effect on cell viability and tumor formation in animals. Results of both cell experiments and in-vivo experiments prove that the inhibition effect on glioblastomas of the compound represented by formula A is close to, or even higher than, that of crizotinib. Particularly, the molecular weight of crizotinib is greater than that of the compound represented by formula A, so that it is more difficult for crizotinib to pass through blood brain barrier, and less crizotinib can reach glioblastomas and limited role can be played. Moreover, crizotinib is a double target medicine. Research shows that crizotinib inhibits ALK while inhibiting c-Met, and therefore has a relatively large side effect. Comparatively, the compound represented by formula A only targets to c-Met, so that the side effect is smaller.

Particularly, experiments prove that the compound represented by formula A has a more significant effect of inhibiting secondary glioblastomas which express specific fusion protein, and the effect is far beyond that of similar compounds or known therapeutic medicines. Through detection on whether or not the fusion protein is expressed or the fusion transcript as mentioned is present in a glioblastoma, the sub-type of glioblastomas expressing the fusion protein or containing the fusion transcript can be distinguished from other glioblastomas, and then the compound represented by formula A is adopted to give effective treatment, thereby realizing personalized precision treatment on patients with glioblastomas, and radically solving the problem of poor prognosis caused by such specific type of glioblastomas. At the same time, based on the action mechanism of the compound represented by formula A, side effects can be avoided, and pains of patients can be relieved, making the treatment with the medicament safer and more efficient. Finally, cost benefits of disease treatment and prognosis are improved.

BRIEF DESCRIPTION OF THE DRAWINGS

Hereinafter, embodiments of the present invention will be described with reference to the accompanying drawings in detail, in which.

DETAILED DESCRIPTION OF PREFERRED EMBODIMENTS

Figure 1:
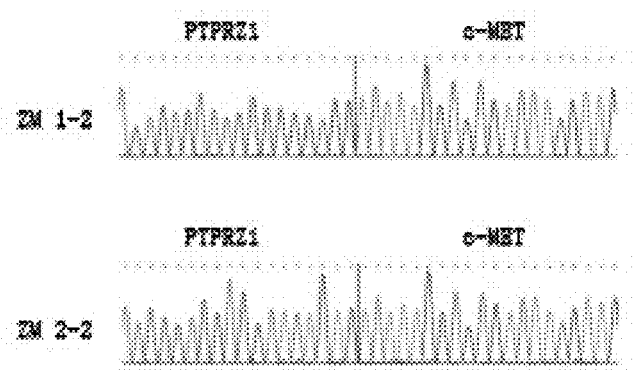
FIG. 1 shows cDNA sequencing results of a fusion protein (ZM1-2) as shown by SEQ ID NO: 3 and a fusion protein (ZM2-2) as shown by SEQ ID NO: 4 provided by the present invention.

Hereinafter the present invention is to be described with reference to specific Examples. Those skilled in the art can understand that those Examples are merely used to describe the present invention instead of limiting the scope of the present invention in any way.

Unless otherwise specified, methods in the following Examples are conventional methods. Raw medicinal materials and reagent materials etc. used in the following Examples are all commercially available products, unless otherwise specified.

Example 1: Obtaining RNAs and cDNAs of Glioblastomas 80 glioblastoma samples were collected through operations that conformed to standards of the Medical Ethics Committee. Each sample was collected with a written consent from the patient who donated the sample and the doctor of the patient. The gender, age and disease type of the samples are shown in Table 1.

TABLE 1

| Case No. | Gender | Age | Glioblastoma type |
|---|---|---|---|
| 1 | M | 44 | Primary |
| 2 | F | 59 | Primary |
| 3 | F | 56 | Primary |
| 4 | F | 48 | Primary |
| 5 | M | 64 | Primary |
| 6 | M | 66 | Primary |
| 7 | M | 59 | Primary |
| 8 | F | 62 | Primary |
| 9 | M | 42 | Primary |
| 10 | M | 81 | Primary |
| 11 | M | 60 | Primary |
| 12 | M | 29 | Primary |
| 13 | M | 26 | Primary |
| 14 | M | 47 | Primary |
| 15 | M | 42 | Primary |
| 16 | F | 43 | Primary |
| 17 | F | 40 | Primary |
| 18 | M | 27 | Primary |
| 19 | M | 42 | Primary |
| 20 | F | 37 | Primary |
| 21 | M | 45 | Primary |
| 22 | M | 54 | Primary |
| 23 | F | 47 | Primary |
| 24 | M | 33 | Primary |
| 25 | M | 63 | Primary |
| 26 | M | 34 | Primary |
| 27 | M | 18 | Primary |
| 28 | M | 33 | Primary |
| 29 | M | 30 | Primary |
| 30 | M | 49 | Primary |
| 31 | M | 43 | Primary |
| 32 | F | 28 | Primary |
| 33 | M | 42 | Primary |
| 34 | F | 62 | Primary |
| 35 | M | 48 | Primary |
| 36 | F | 51 | Primary |
| 37 | F | 40 | Primary |
| 38 | F | 24 | Primary |
| 39 | F | 49 | Primary |
| 40 | M | 51 | Primary |
| 41 | F | 55 | Primary |
| 42 | M | 38 | Primary |
| 43 | M | 54 | Primary |
| 44 | F | 60 | Primary |
| 45 | F | 37 | Primary |
| 46 | F | 59 | Primary |
| 47 | M | 54 | Primary |
| 48 | M | 52 | Primary |
| 49 | M | 46 | Primary |
| 50 | M | 56 | Primary |
| 51 | M | 60 | Primary |
| 52 | F | 63 | Primary |
| 53 | M | 44 | Primary |
| 54 | F | 25 | Primary |
| 55 | M | 42 | Primary |
| 56 | M | 51 | Primary |
| 57 | M | 45 | Primary |
| 58 | F | 50 | Primary |
| 59 | M | 61 | Primary |
| 60 | M | 33 | Secondary |
| 61 | M | 8 | Secondary |
| 62 | M | 42 | Secondary |
| 63 | M | 29 | Secondary |
| 64 | M | 29 | Secondary |
| 65 | F | 40 | Secondary |
| 66 | M | 44 | Secondary |
| 67 | M | 33 | Secondary |
| 68 | M | 27 | Secondary |
| 69 | F | 37 | Secondary |
| 70 | F | 56 | Secondary |
| 71 | F | 31 | Secondary |
| 72 | M | 45 | Secondary |
| 73 | F | 34 | Secondary |
| 74 | M | 54 | Secondary |
| 75 | M | 46 | Secondary |
| 76 | M | 18 | Secondary |
| 77 | M | 38 | Secondary |
| 78 | M | 48 | Secondary |
| 79 | M | 53 | Secondary |
| 80 | M | 51 | Secondary |

A RNA extraction kit (purchased from Qiagen) was used to extract total mRNA of each of the glioblastoma samples according to instructions therein. The integrity of the total mRNAs was detected using an analyzer, and it was confirmed that RIN (RNA Integrity Number) of the total mRNA from each sample was greater than 7.0.

A reverse transcription kit (RevertAid First Strand cDNA Synthesis Kit, K1622, purchased from Invitrogen) was used to perform reverse transcription on a 20 μl reaction system according to instructions therein by taking the total mRNA from each sample as a template, thereby synthesizing a double-strand cDNA for each sample.

Example 2: Detection of Fusion Proteins According to the Present Invention in Glioblastomas The double-strand cDNA of each sample prepared in Example 1 was taken as a template and amplified using the following primer sequences:

```
Forward primer:
                              SEQ ID NO: 11
ATGCGAATCCTAAAGCGTTTCCTCG Reverse primer:
                              SEQ ID NO: 12
CTATGATGTCTCCCAGAAGGAGGCT
```

20 μl amplification system included: 10 μM forward primer, 1 μl; 10 μM reverse primer, 1 μl; 100 ng template; 2× Phusion Master Mix (NEB, product No. M0531), 10 μl; and nuclease-free water, making up to 20 μl.

PCR program setting included: 98° C. for 30 sec; 98° C. for 10 sec, 60° C. for 30 sec, and 72° C. for 1.5 min, 30 cycles in total; 72° C. for 5 min; maintained at 12° C.

PCR products were analyzed by 1% agarose gel electrophoresis, and generated bands were recovered with a DNA gel recovery kit (QIAquick PCR purification kit, purchased from Qiagen) and then cloned to a T vector (pGEM-T easy vector, purchased from Promega), and was sequenced with a DNA sequencer (ABI Prism 3730×1 DNA Sequencer, purchased from Applied Biosystems).

Sequencing results showed that two different nucleotide sequences were obtained through amplification. They have 66 different nucleotides, and are respectively as shown by SEQ ID NO: 7 and SEQ ID NO: 8. The sequencing results of the nucleotide sequences are shown in FIG. 1. Besides, the genomic DNA sequences of fusion protein ZM3-2 and fusion protein ZM8-2 were found through sequencing the whole-genome DNAs of certain samples.

Based on sample sources, it was found that No. 60 sample, No. 64 sample, No. 77 sample, No. 78 sample and No. 80 sample listed in Table 1 had cDNAs or genomic DNAs of corresponding fusion proteins: fusion protein ZM1-2 was found in No. 60 sample, fusion protein ZM2-2 was found in both No. 64 sample and No. 78 sample, fusion protein ZM3-2 was found in No. 77 protein, and fusion protein ZM8-2 was found in No. 80 sample. Results showed that the fusion proteins and the encoding RNAs or genomic DNAs thereof according to the present invention were specifically present in one part of glioblastomas, not in another part of glioblastomas, and nearly all were found in secondary glioblastomas.

Figure 2:
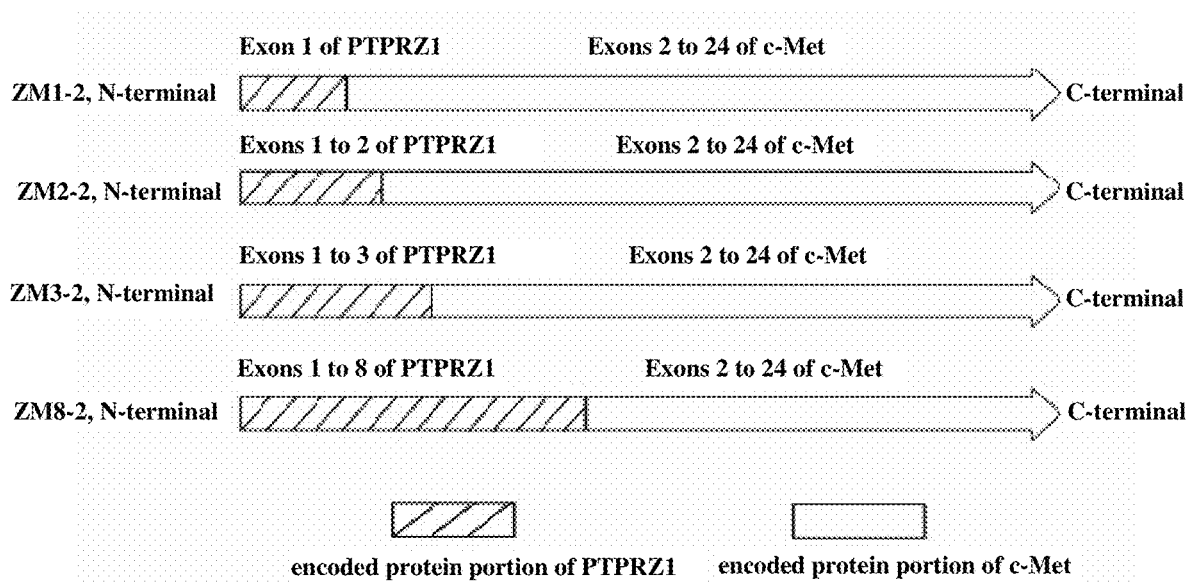
FIG. 2 shows structures of the fusion proteins provided by the present invention.

Thus amino acid sequences of the fusion proteins are obtained, as shown by SEQ ID NO: 3 (fusion protein ZM1-2), SEQ ID NO: 4 (fusion protein ZM2-2), SEQ ID NO: 5 (fusion protein ZM3-2), and SEQ ID NO: 6 (fusion protein ZM8-2). Through sequence alignment, it was found that those four fusion proteins were all formed by fusing part of PTPRZ1 protein to almost the entire c-Met protein, from N-terminal to C-terminal. Particularly, fusion protein ZM1-2 was obtained by fusing exon 1 of PTPRZ1 to exons 2 to 24 of c-Met, fusion protein ZM2-2 was obtained by fusing exons 1 to 2 of PTPRZ1 to exons 2 to 24 of c-Met, fusion protein ZM3-2 was obtained by fusing exons 1 to 3 of PTPRZ1 to exons 2 to 24 of c-Met, and fusion protein ZM8-2 was obtained by fusing exons 1 to 8 of PTPRZ1 to exons 2 to 24 of c-Met; and, the four fusion proteins all did not contain portion corresponding to the promoter and exon 1 of c-Met (non-function element). Therefore, it was speculated that fusion genes were transcribed with the promoter of PTPRZ1. The structural representations of the four fusion genes are shown in FIG. 2.

Besides, clinical research has found that, the median survival of the glioblastoma cases with the fusion proteins as described in the present invention was 127 days, shorter than the median survival of reported glioblastoma cases (248 days). Thus, it is proved that among secondary glioblastomas, the sub-type of glioblastomas that expresses fusion proteins as described in the present invention have poorer prognosis.

Example 3: Immunoblotting Verification of Fusion Proteins in Glioblastomas

Total proteins of the 80 glioblastoma samples collected in Example 1 were subjected to immunoblotting verification of fusion proteins.

The antibody used in the immunoblotting verification was an antibody against human c-Met protein (rabbit antibody, purchased from Abcam, product No.: ab51067). The molecular weight of a non-fusion human c-Met protein was 145 kDa, while the molecular weight of a fusion protein was larger. Immunoblotting operations were performed according to instructions of the antibody and instructions of the immunoblotting kit.

Figure 3:
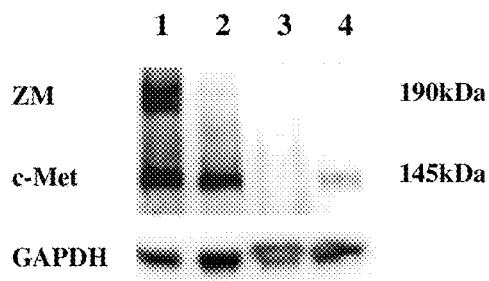
FIG. 3 shows immunoblotting results of fusion proteins provided by the present invention in Example 3, in which Lane 1 is fusion protein ZM8-2, Lane 2 is fusion protein ZM2-2, and Lanes 3 and 4 are respectively references.

Immunoblotting results showed that the obtained immunoblotting bands were consistent with the results in Example 2: immunoblotting bands were found in No. 60, No. 64, No. 77, No. 78 and No. 80 samples among samples listed in Table 1 (all were secondary glioblastoma samples). FIG. 3 shows the immunoblotting results of ZM8-2 and ZM2-2, in which the molecular weight of ZM8-2 was about 190 kDa, and the molecular weight of ZM2-2 was close to that of a non-fusion human c-Met protein, as shown by approximately overlapped immunoblotting bands.

Thus it can be known that the fusion proteins as described in the present invention are specifically expressed in one part of glioblastomas, not in another part of glioblastomas. Therefore, glioblastomas can be classified into a sub-type of glioblastomas which expresses the fusion proteins and the sub-type of glioblastomas which does not express the fusion proteins.

Example 4: Determination of Inhibitory Activity of the Compound Represented by Formula A on Glioblastoma Cell Proliferation The compound represented by formula A and crizotinib as well as compounds represented by formulas B to H that respectively have a structure similar to the structure of formula A were employed to carry out the experiment of testing the activity of inhibiting glioblastoma cell proliferation.

The compounds represented by formulas A-H were synthesized by steps and scheme disclosed in Chinese patent application publication CN103122000A.

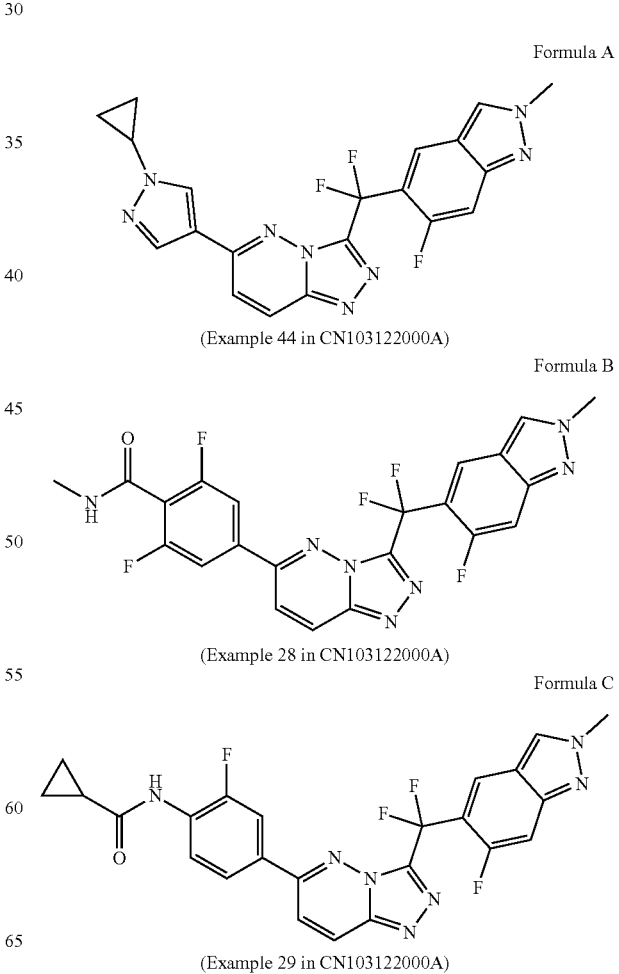

Formula A (Example 44 in CN103122000A)

Formula B (Example 28 in CN103122000A)

Formula C (Example 29 in CN103122000A)

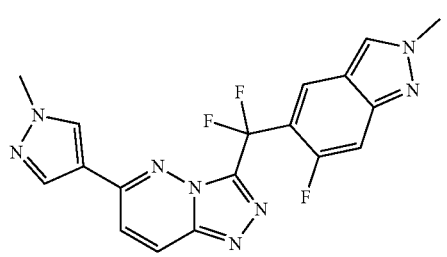

(Example 37 in CN103122000A)

Formula D

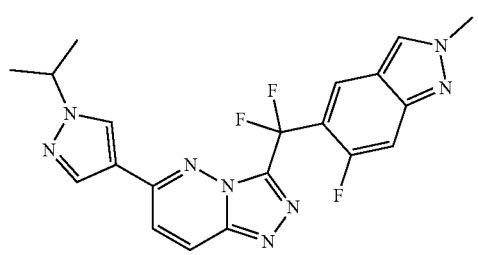

(Example 38 in CN103122000A)

Formula E

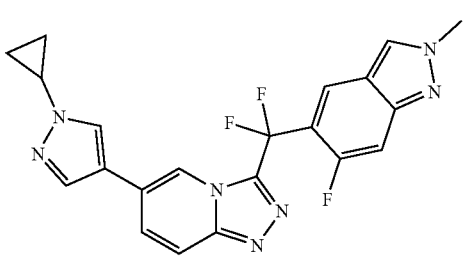

(Example 46 in CN103122000A)

Formula F

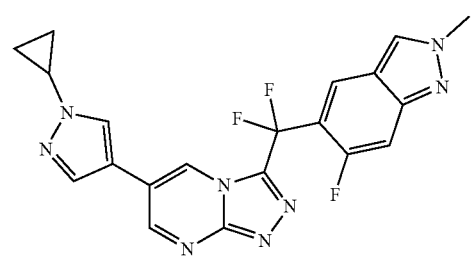

(Example 47 in CN103122000A)

Formula G

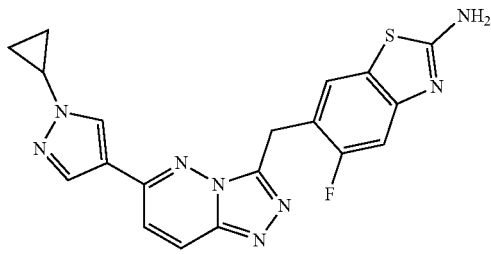

(Example 49 in CN103122000A)

Formula H

Crizotinib (CRIZOTINIB; PF-02341066): product No. S1068, purchased from Selleck, USA.

Figure 4:
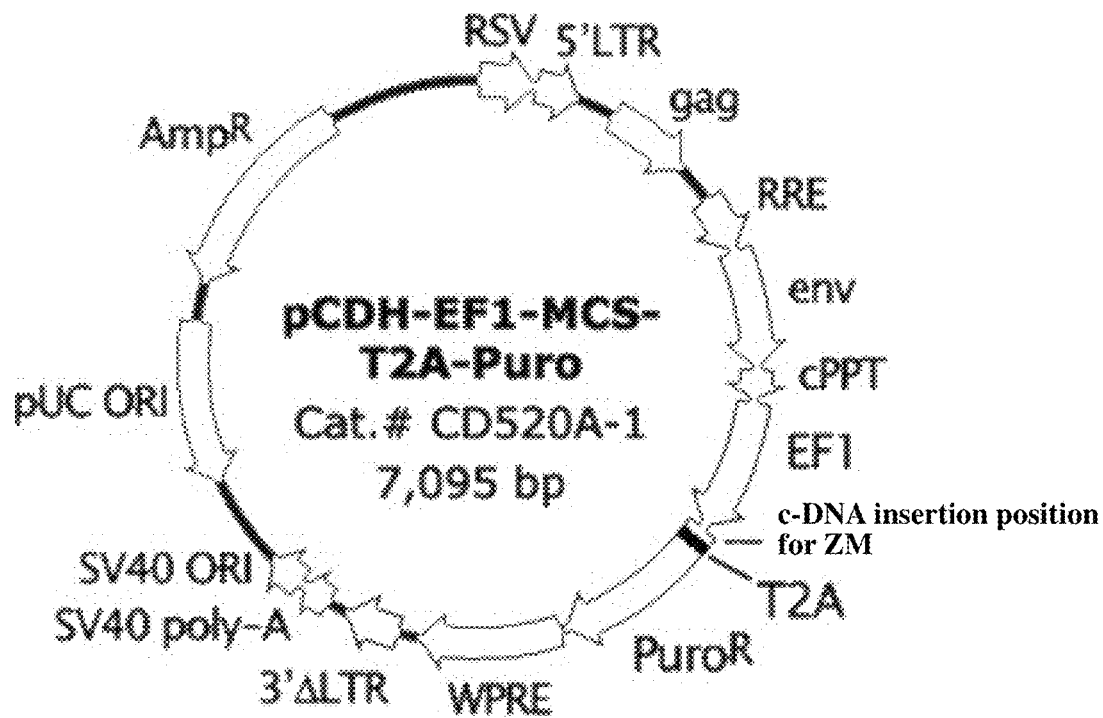
FIG. 4 is a structural representation of a lentiviral vector PCDH-EF1-MCS-T2A-Puro, in which the insertion position for the sequence encoding the fusion protein is shown.

First, a lentiviral vector PCDH (PCDH-EF1-MCS-T2A-Puro, SBI, product No.: CD510B-1, structure shown in FIG. 4) was used, and the nucleotide sequence as shown by SEQ ID NO: 7 or SEQ ID NO: 8 was cloned into the vector according to the instructions thereof, to prepare expression vectors which expressed fusion proteins respectively represented by SEQ ID NO: 3 and SEQ ID NO: 4. The expression vectors were respectively named and marked as "PCDH-ZM1-2" and "PCDH-ZM2-2". Then, a viral packaging plasmid (SBI, product No. LV500A-1) was used to co-infect 293T cells with one of the vectors to prepare a lentivirus. The same method was performed to package the lentiviral vector PCDH and co-infect 293T cells, to prepare a lentivirus with the blank vector, which was named as "PCDH-blank".

A human glioma cell line U87, which did not express any one of the fusion proteins provided by the present invention, was purchased from the Cell Bank of Chinese Academy of Medical Sciences. The U87 cells were infected with any of the lentiviruses as prepared above and screened by applying puromycin (0.5 μg/mL for screening, and 0.2 μg/mL for maintenance) to establish cell models which stably expressed the fusion proteins. The cell models were verified for the expression of the fusion proteins and the transcription of the fusion genes by immunoblotting and reverse transcription PCR, and cell lines which stably expressed fusion proteins ZM1-2 and ZM2-2 respectively were obtained finally and named as "PCDH-ZM1-2 expressing cells" and "PCDH-ZM2-2 expressing cells" respectively. Similarly, U87 cells were infected with the lentivirus PCDH-blank with the blank vector to obtain "PCDH-blank expressing cells" as a blank reference.

Those U87 cells which were cultured in a large dish and were in a logarithmic stage were washed once with sterile PBS, and then digested with 0.25% trypsin for 2 min. After all cells were digested to detach, complete DMEM medium containing 10% fetal bovine serum (FBS) was used to stop the digestion. The cells were counted and the cell concentration was adjusted to 20,000 cells/ml. Then, the cells were seeded into a Corning 96-well plate (2,000 cells/well) using a multi-channel pipette, and incubated in a 5% $CO_2$ incubator at 37° C. for 24 hours. The compounds to be tested (crizotinib and the compounds represented by formulas A to H) were respectively dissolved in DMSO to prepare stock solutions, and then the stock solutions and the complete medium were used to prepare solutions with different concentrations of medicaments (0, 5, 10, 20, 40, 60, 80, 100 μM). The cells were incubated in the incubator for additional 72 hours, and then 20 μl of 3-(4,5-dimethylthiazole-2)-2,5-diphenyl tetrazolium bromide (MTT) was added into each well. After 1-3 hours in the incubator, the absorbance at 490 nm was determined using a microplate reader. The inhibition rate corresponding to each concentration was calculated, and the value of $IC_{50}$ was calculated with GraphPad software. Results are shown in Table 2.

TABLE 2

| Cell model | | U87 initial cells | Blank reference | PCDH-ZM1-2 expressing cells | PCDH-ZM2-2 expressing cells |
| --- | --- | --- | --- | --- | --- |
| Inhibitory activities ($IC_{50}$, μM) of tested compounds on cells | Crizotinib | 2.99 | 3.27 | 8.26 | 9.76 |
| | Formula A | 3.51 | 2.85 | 1.34 | 1.83 |
| | Formula B | 8.15 | 6.02 | 7.63 | 5.59 |
| | Formula C | 4.78 | 5.79 | 9.45 | 12.76 |
| | Formula D | 5.56 | 4.93 | 5.22 | 7.21 |
| | Formula E | 17.25 | 21.64 | 32.64 | 21.88 |
| | Formula F | 64.37 | 58.82 | 90.33 | 125.29 |
| | Formula G | 9.07 | 9.25 | 6.75 | 15.25 |
| | Formula H | 25.38 | 19.35 | 23.31 | 45.12 |

From Table 2 it can be known that, in the human glioma cell line U87 itself and the blank reference cell line U87, compared with the compounds represented by formulas F to G that have similar structures, the compound represented by formula A achieves a more significantly potent effect of inhibiting cell viability, and achieves an inhibition effect on proliferation similar to, or even higher than that of crizotinib.

In addition, during experiments, it was found that glioblastomas with expression of fusion proteins ZM1-2 and ZM2-2 obviously proliferated faster. Among the cells, the cell viability could only be inhibited by the compound represented by formula A, and the inhibitory effects on cell viability of the compounds represented by formulas B to H and the crizotinib were obviously inferior to that of the compound represented by the formula A.

Example 5: Determination of Inhibitory Activity of the Compound Represented by Formula A of In-Vivo Tumor Formation of Glioblastomas An experiment of inhibiting in-vivo tumor formation of glioblastoma was performed with the compound represented by formula A and crizotinib.

(1) Experiment of Inhibition on Tumor Growth

First, a tumor-bearing mouse model was established. BALB/c (nu/nu) maternal nude mice, aged 6-8 weeks, with a weight of about 16-18 g were purchased from Vital River. "PCDH-blank expressing cells" and "PCDH-ZM2-2 expressing cells" prepared in Example 4 were prepared into suspensions of $10^7$ cells/ml with PBS respectively. Nude mice sterilized with 75% ethanol were subcutaneously injected with 100 µl of the cell suspensions at the right scapular area, in which the PCDH-blank expressing cells were injected into seven nude mice, and PCDH-ZM2-2 expressing cells were injected into 21 nude mice. About 2-3 days after subcutaneous inoculation, began to observe the formation of solid tumors, and the tumors were found to be formed after about 15 days. The tumor size and variations in mouse weight were measured twice a week. The tumor-bearing mice obtained by injection with the "PCDH-blank expressing cells" were named as "vector mice (1)", and the tumor-bearing mice obtained by injection with "PCDH-ZM2-2 expressing cells" were named as "ZM2-2 mice (1)".

Figure 5:
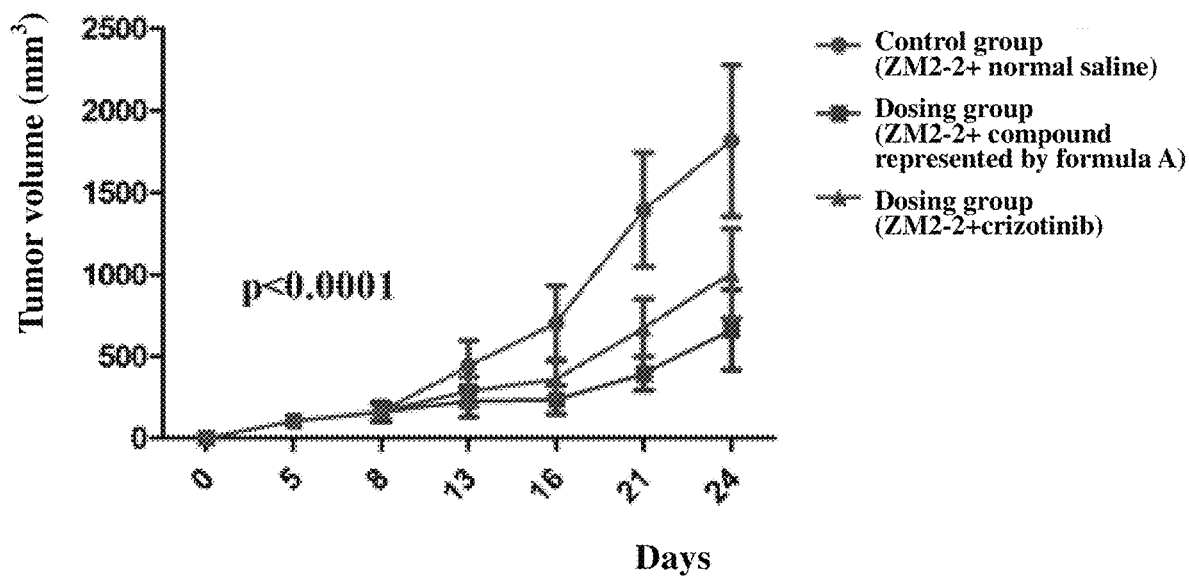
FIG. 5 shows experimental results of inhibition on in-vivo tumor growth in Example 5.

When the tumors grew to have a volume of about 100 mm$^3$, the ZM2-2 mice (1) were divided into three groups according to mean tumor size, including a group of 7 mice which were administered with the compound represented by formula A, a group of 7 mice which were administered with crizotinib, and a control group of 7 mice. The former two groups were given with the compound represented by formula A in a dose of 10 mg/KG/day or crizotinib in a dose of 50 mg/KG/day by gavage. The two medicaments were prepared into suspensions with normal saline respectively and given once a day with continuously stirring for continuous administration. The control group was gavaged with normal saline. The tumor size and variations in mouse weight were measured twice a week. The tumor diameter was measured with a vernier caliper, and the equation for calculating tumor volume was: tumor volume=0.5*Length*Width$^2$. Variations in tumor size are shown in FIG. 5. Results showed that, the compound represented by formula A could significantly inhibit the growth of tumors in ZM2-2 mice (1), and the inhibition effect was potent than that of crizotinib.

(2) Experiment of Survival of Mice

First, a tumor-bearing mouse model was established. "PCDH-blank expressing cells" and "PCDH-ZM2-2 expressing cells" prepared in Example 4 were prepared into suspensions of $10^5$ cells/5 µl with PBS respectively. Nude mice sterilized with 75% ethanol were inoculated with 100 µl of the cell suspensions. The cell inoculation position (2 mm away on the right side of anterior fontanel, and 2 mm backward) was determined using a brain stereotaxic apparatus for mouse; the injection depth was 3.5 mm and then elevated by 0.6 mm; and 5 µl of cell solutions respectively was injected to each mouse. After injection, the mice were kept still for 1 min, and then received a conventional skin closure. After intracranial tumors were observed, the tumor-bearing mice obtained with the "PCDH-blank expressing cells" were named as "vector mice (2)", and the tumor-bearing mice obtained with the "PCDH-ZM2-2 expressing cells" were named as "ZM2-2 mice (2)".

The brains of the mice were detected through nuclear magnetic resonance imaging. It was found that, the intracranial tumors of the vector mice (2) were obviously smaller than the intracranial tumors of the ZM2-2 mice (2). Thus it is proved that, the expression of fusion proteins provided by the present invention resulted in obvious enhancement in the tumor formation of glioblastomas in mice. Results are shown in panel 7A and panel 7B, respectively.

Figure 6:
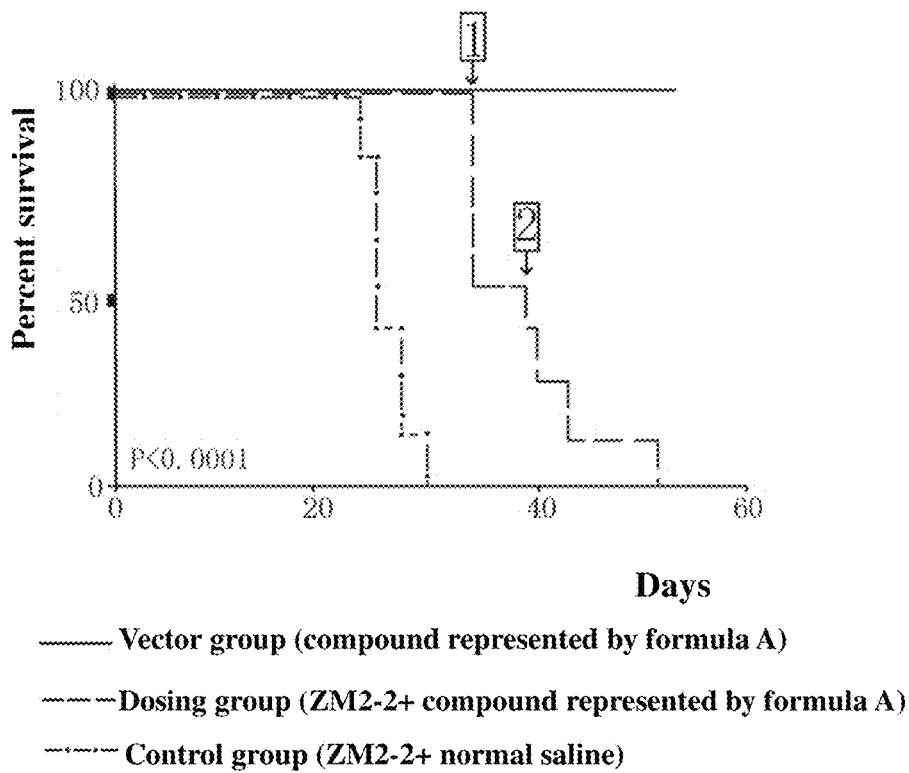
FIG. 6 shows results of mice survival experiment in Example 5.
Figure 7:
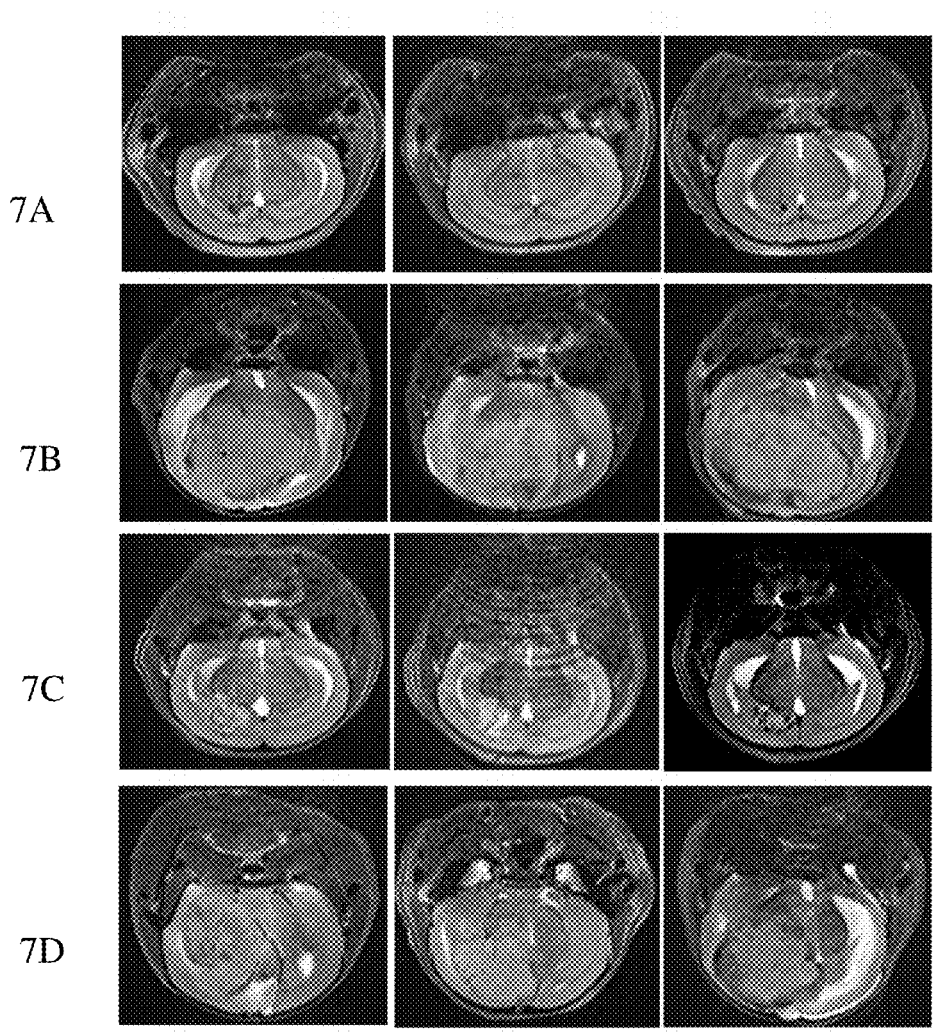
FIG. 7 shows cerebral magnetic resonance imaging results of an in-vivo tumor formation experiment of glioblastoma in Example 5, in which panel 7A shows a brain image of a vector mouse (2) obtained by modeling, panel 7B shows a brain image of a ZM2-2 mouse (2) obtained by modeling, panel 7C shows a brain image of the ZM2-2 mouse (2) on the 16th day after the compound represented by formula A was administered for the first time, and panel 7D shows a brain image of the ZM2-2 mouse (2) 10 days since the compound administration had been stopped on the 16th day after the compound represented by formula A was administered for the first time.

8 Vector mice (2) and 8 ZM2-2 mice (2) were respectively administered with the compound represented by the formula A at a dose of 50 mg/KG weight/day. The compound was administrated once a day by gavage. At the same time, another group of 8 ZM2-2 mice (2) were given with normal saline, as a control group. The experiment lasted for over 6 weeks. Results showed that the ZM2-2 mice (2) only given with normal saline died gradually since the 20th day, while the vector mice (2) given with the compound represented by formula A all survived, and the administration of the compound represented by the formula A obviously prolonged the survival time of the ZM2-2 mice (2), as shown in FIG. 6.

The brains of ZM2-2 mice (2) given with the compound represented by formula A were detected by nuclear magnetic resonance imaging on the 16th day after the compound represented by formula A was administered for the first time. It was found that the intracranial tumor obviously became smaller. See results in panel 7C. Similarly, it is proved that the compound represented by formula A can obviously inhibit the growth of tumors in the ZM2-2 mice.

Another 8 ZM2-2 mice (2) were also administered with the compound represented by formula A at a dose of 50 mg/KG weight/day. The compound was administrated once a day by gavage. Then, the compound administration was stopped on the 16th day after the first administration, and the brains were detected through nuclear magnetic resonance imaging on the 10th day after the compound withdrawal. It was found that the tumors resumed rapid growth. Results are shown in panel 7D.

According to the above experimental results, it can be seen that, the compound represented by formula A can significantly inhibit the growth of the glioblastomas which express the fusion proteins provided by the present invention and prolong the survival of patients, and glioblastomas were apt to recurrence after withdrawal of the compound. The tumor inhibition effect of the compound represented by formula A is even stronger than that of crizotinib, and so the compound can be used as a substitute for crizotinib.

Moreover, it has been proved that the median survival period of the cases of glioblastomas which express the fusion proteins of the present invention is shorter than that of the cases of other reported glioblastomas, which means that among glioblastomas, cases of glioblastomas which express the fusion proteins have a poorer prognosis. For such sub-type of glioblastoma with poorer prognosis, the compound represented by formula A can achieve a better therapeutic effect in comparison with other compounds capable of serving as c-Met inhibitors as well as crizotinib.

The above description for the embodiments of the present invention is not intended to limit the present invention, and those skilled in the art can make various changes and variations according to the present invention, which are within the protection scope of the present invention without departing from the spirit of the same.

What is claimed is:

1. A method for treating glioblastoma, comprising:

1) detecting whether or not a fusion protein is expressed or a fusion transcript is contained in a glioblastoma sample from a patient suffering from glioblastoma, and/or detecting the content of the fusion protein or the fusion transcript in the sample, the fusion protein being formed by fusing a protein portion translated from exon 1, exons 1 to 2, exons 1 to 3 or exons 1 to 8 of PTPRZ1 to a protein portion translated from exons 2 to 24 of c-Met, in which the protein portion of PTPRZ1 is located at the N-terminal of the protein portion of c-Met, and the fusion transcript is formed by connecting a RNA portion which is transcribed from exon 1, exons 1 to 2, exons 1 to 3 or exons 1 to 8 of PTPRZ1 and a RNA portion which is transcribed from exons 2 to 24 of c-Met, in which the RNA portion of PTPRZ1 is located at the 5-terminal of the RNA portion of c-Met; and 2) administering a compound represented by formula A or a pharmaceutical composition containing the compound represented by formula A to the patient if the sample contains the fusion protein or the fusion transcript or if the content of the fusion protein or the fusion transcript is higher than that in a normal subject or in any other relevant sample:

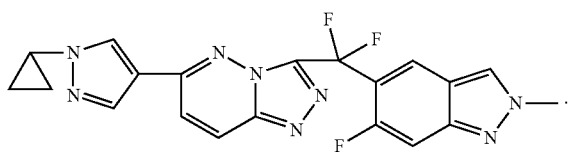

Formula A

2. The method according to claim 1, wherein the glioblastoma is a secondary glioblastoma.

3. The method according to claim 1, wherein the fusion protein comprises the amino acid sequence as shown by SEQ ID NO: 1.

4. The method according to claim 1, wherein the fusion protein further comprises the amino acid sequence as shown by SEQ ID NO: 2.

5. The method according to claim 1, wherein the fusion protein comprises the amino acid sequence as shown by SEQ ID NO: 1 and the amino acid sequence as shown by SEQ ID NO: 2 at the N-terminal thereof.

6. The method according to claim 2, wherein the fusion protein comprises the amino acid sequence as shown by SEQ ID NO: 1.

7. The method according to claim 2, wherein the fusion protein further comprises the amino acid sequence as shown by SEQ ID NO: 2.

8. The method according to claim 2, wherein the fusion protein comprises the amino acid sequence as shown by SEQ ID NO: 1 and the amino acid sequence as shown by SEQ ID NO: 2 at the N-terminal thereof.

9. The method according to claim 1, wherein the fusion protein comprises the amino acid sequence as shown by SEQ ID NO: 3, SEQ ID NO: 4, SEQ ID NO: 5 or SEQ ID NO: 6.

10. The method according to claim 1, wherein the amino acid sequence of the fusion protein is as shown by SEQ ID NO: 3, SEQ ID NO: 4, SEQ ID NO: 5 or SEQ ID NO: 6.

11. The method according to claim 1, wherein the fusion transcript comprises a RNA sequence encoding the amino acid sequence as shown by SEQ ID NO: 1.

12. The method according to claim 1, wherein the fusion transcript further comprises a RNA sequence encoding the amino acid sequence as shown by SEQ ID NO: 2.

13. The method according to claim 1, wherein the fusion transcript comprises a RNA sequence encoding the amino acid sequence as shown by SEQ ID NO: 1, and a RNA sequence encoding the amino acid sequence as shown by SEQ ID NO: 2 at the 5-terminal thereof.

14. The method according to claim 2, wherein the fusion transcript comprises a RNA sequence encoding the amino acid sequence as shown by SEQ ID NO: 1.

15. The method according to claim 2, wherein the fusion transcript further comprises a RNA sequence encoding the amino acid sequence as shown by SEQ ID NO: 2.

16. The method according to claim 2, wherein the fusion transcript comprises a RNA sequence encoding the amino acid sequence as shown by SEQ ID NO: 1, and a RNA sequence encoding the amino acid sequence as shown by SEQ ID NO: 2 at the 5-terminal thereof.

17. The method according to claim 1, wherein the fusion transcript comprises a RNA sequence encoding the amino acid sequence as shown by SEQ ID NO: 3, SEQ ID NO: 4, SEQ ID NO: 5 or SEQ ID NO: 6.

18. The method according to claim 1, wherein the nucleotide sequence of the fusion transcript comprises a RNA sequence encoding the amino acid sequence as shown by SEQ ID NO: 3, SEQ ID NO: 4, SEQ ID NO: 5 or SEQ ID NO: 6.

19. The method according to claim 2, wherein the fusion protein comprises the amino acid sequence as shown by SEQ ID NO: 3, SEQ ID NO: 4, SEQ ID NO: 5 or SEQ ID NO: 6.

20. The method according to claim 2, wherein the amino acid sequence of the fusion protein is as shown by SEQ ID NO: 3, SEQ ID NO: 4, SEQ ID NO: 5 or SEQ ID NO: 6.

21. The method according to claim 2, wherein the fusion transcript comprises a RNA sequence encoding the amino acid sequence as shown by SEQ ID NO: 3, SEQ ID NO: 4, SEQ ID NO: 5 or SEQ ID NO: 6.

22. The method according to claim 2, wherein the nucleotide sequence of the fusion transcript comprises a RNA sequence encoding the amino acid sequence as shown by SEQ ID NO: 3, SEQ ID NO: 4, SEQ ID NO: 5 or SEQ ID NO: 6.

* * * * *